United States Patent
Ghose et al.

(10) Patent No.: US 11,988,568 B2
(45) Date of Patent: May 21, 2024

(54) SENSOR BASED WEARABLE FABRIC DESIGN FOR IDENTIFYING DISTORTION IN MOVEMENTS AND QUANTIFYING RANGE OF MOTION

(71) Applicant: Tata Consultancy Services Limited, Mumbai (IN)

(72) Inventors: Avik Ghose, Kolkata (IN); Parama Pal, Bangalore (IN); Murali Poduval, Mumbai (IN)

(73) Assignee: Tata Consultancy Services Limited, Mumbai (IN)

( * ) Notice: Subject to any disclaimer, the term of this patent is extended or adjusted under 35 U.S.C. 154(b) by 849 days.

(21) Appl. No.: 17/014,554

(22) Filed: Sep. 8, 2020

(65) Prior Publication Data
US 2021/0293634 A1 Sep. 23, 2021

(30) Foreign Application Priority Data
Mar. 20, 2020 (IN) .............................. 202021012085

(51) Int. Cl.
*G01L 1/24* (2006.01)
*A41D 1/00* (2018.01)
(Continued)

(52) U.S. Cl.
CPC .............. *G01L 1/246* (2013.01); *A41D 1/002* (2013.01); *A61B 5/0002* (2013.01);
(Continued)

(58) Field of Classification Search
CPC .............................. G01L 1/246; A61B 5/1121
See application file for complete search history.

(56) References Cited

U.S. PATENT DOCUMENTS 7,903,907 B1 * 3/2011 Park ........................ G01L 1/246
385/100
9,498,128 B2 11/2016 Jayalath et al.
(Continued)

FOREIGN PATENT DOCUMENTS

| CA | 2141525 C | 1/2002 | |
|----|-----------|--------|---|
| FR | 2865539 A1 * | 7/2005 | ............. G01L 1/246 |
| WO | WO2000067539 A1 | 11/2000 | |

OTHER PUBLICATIONS

Wang, Zhengyue et al., Deformation behaviors of three-dimensional auxetic spacer fabrics, Textile Research Journal, Feb. 21, 2014, pp. 281-288, SAGE Publications, http://citeseerx.ist.psu.edu/viewdoc/download?doi=10.1.1.941.4050&rep=rep1&type=pdf.

*Primary Examiner* — Clayton E. LaBalle
*Assistant Examiner* — Diana Hancock
(74) *Attorney, Agent, or Firm* — Finnegan, Henderson, Farabow, Garrett & Dunner, LLP

(57) ABSTRACT

This disclosure relates generally to a sensor based wearable fabric design for identifying distortion in movements and quantifying range of motion. Accurate quantification of multi-axial range of motion involved in complex movements of human body parts is challenging. The disclosure discloses a system and method providing a wearable fabric comprising a plurality of honey-comb structure with a plurality of adjacently placed hexagon structures. An optical sensor unit is placed on each side of each hexagon structure comprised in the plurality of honey-comb structures. A deformation of the plurality of sides of hexagon structure is determined to generate signatures of movement patterns of one or more body parts of a subject. Further, a comparison of generated signatures with stored signatures of the movement patterns is performed to determine an error indicative of a distortion in the movement patterns. The system and method accurately quantify range of motion with increased measurement accuracy.

13 Claims, 23 Drawing Sheets

(51) Int. Cl.
    *A61B 5/00*        (2006.01)
    *A61B 5/11*        (2006.01)
    *A41B 11/00*      (2006.01)
    *A41D 1/089*      (2018.01)
    *A41D 19/00*      (2006.01)
    *A44C 5/00*       (2006.01)
    *A61B 34/20*      (2016.01)

(52) U.S. Cl.
    CPC .......... *A61B 5/1121* (2013.01); *A61B 5/6804* (2013.01); *A61B 5/742* (2013.01); *A61B 5/746* (2013.01); *A41B 11/00* (2013.01); *A41B 2400/32* (2013.01); *A41D 1/089* (2018.01); *A41D 19/0027* (2013.01); *A41D 2400/32* (2013.01); *A44C 5/0015* (2013.01); *A44C 5/0023* (2013.01); *A61B 2034/2061* (2016.02)

(56) References Cited

U.S. PATENT DOCUMENTS

| | | | |
|---|---|---|---|
| 2005/0146076 A1 | 7/2005 | Alexander et al. | |
| 2015/0309563 A1* | 10/2015 | Connor | A61B 5/1071 |
| | | | 73/865.4 |
| 2016/0349790 A1* | 12/2016 | Connor | G06F 3/017 |
| 2017/0156662 A1* | 6/2017 | Goodall | A61N 2/002 |
| 2017/0198244 A1 | 7/2017 | Göbel et al. | |
| 2017/0354353 A1* | 12/2017 | Kim | G01L 1/246 |

\* cited by examiner

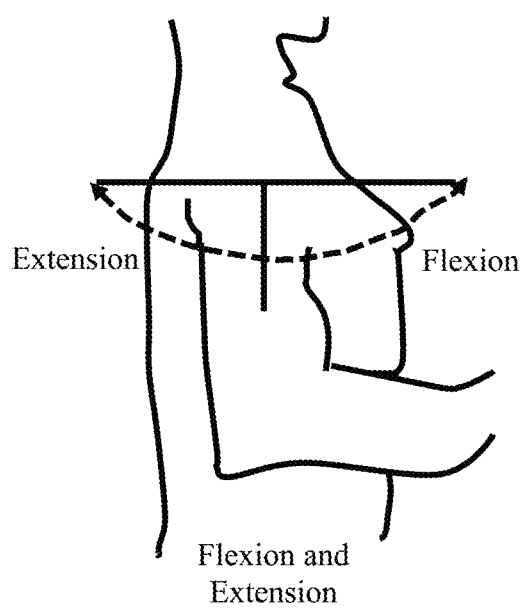
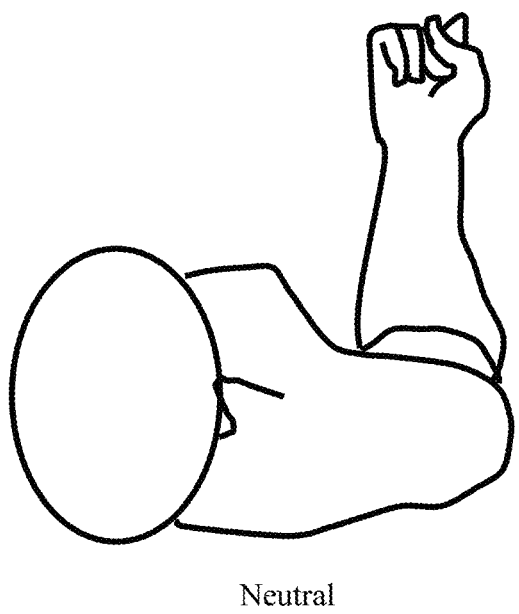
Flexion and Extension
Neutral
FIG. 8A
FIG. 8B

3 Abductions

Extension

Rotation in Abduction

Rotation in neutral

Elevation

SENSOR BASED WEARABLE FABRIC DESIGN FOR IDENTIFYING DISTORTION IN MOVEMENTS AND QUANTIFYING RANGE OF MOTION

PRIORITY CLAIM

This U.S. patent application claims priority under 35 U.S.C. § 119 to: India Application No. 202021012085, filed on Mar. 20, 2020. The entire contents of the aforementioned application are incorporated herein by reference.

TECHNICAL FIELD

The disclosure herein generally relates to wearable fabric, and, more particularly, to sensor based wearable fabric design for identifying distortion in movements and quantifying range of motion.

BACKGROUND

Human range of motion is an important measure used for orthopedic and neurological studies. Clothes are considered as second skin of human body, and like skin the clothes realize all movements made by humans. All body movements cause stretching and contraction of skin in some form. Hence, human body movements can be analyzed in a better way by activating a sensor into a piece of clothing or fabric.

Conventional systems for studying range of motion include gait lab-based assessment which requires a patient to wear a body suit with multiple markers and then use 3D motion capture technology to get accurate point measurements. However, this requires intensive setup and hence huge cost. Conventional systems also utilize gyroscope and accelerometers for recording range of motion. However, the gyroscopes are not very perfect for sensing complex rotation across joints due to non-commutative nature of rotation. One conventional system disclose design of a triboelectric sensor based fabric which can provide sweat monitoring along with movement analysis. However, triboelectric fibers have low durability and are not robust to mechanical and environmental damage.

SUMMARY

Embodiments of the present disclosure present technological improvements as solutions to one or more of the above-mentioned technical problems recognized by the inventors in conventional systems. For example, in one aspect, a processor implemented method for identifying distortion in movement patterns of a subject is provided. The method comprising: detecting deformation of a plurality of sides in a wearable fabric worn by the subject. In an embodiment, the deformation of the plurality of sides is determined based on a difference in frequency of incident light and reflected light by a Fiber Bragg Grating. In an embodiment, the method further comprising generating signatures of movement patterns of one or more parts of body of the subject in accordance with the detected deformation; comparing, the generated signatures with stored signatures of the movement patterns of the one or more parts of body of the subject; determining, an error indicative of distortion in the movement patterns of the one or more parts of body of the subject in accordance with a difference between the generated signatures and the stored signatures. In an embodiment, the signature for a specific movement pattern is generated based on aggregation of information transmitted to a centralized unit 106. In an embodiment, the information is transmitted from the transmitter to centralized unit 106 through at least one of (i) a wireless medium channel or (ii) a wired medium channel. In an embodiment, the error indicative of distortion is used to quantify range of motion of the movement patterns of the one or more body parts of the subject. In an embodiment, the centralized unit 106 provides an alert when the error indicative of distortion exceeds a pre-defined threshold, wherein the alert is displayed in an electronic device.

In another aspect, a system of sensor based wearable fabric design for identifying distortion in movements and quantifying range of motion is provided. The system comprising: a centralized unit; a wearable fabric, comprising: a plurality of honey-comb structures, wherein each of the honey-comb structure comprising a plurality of adjacently placed hexagon structures, wherein each hexagon structure comprising a plurality of optical sensor units with each optical sensor unit placed on each side of the hexagon structure, wherein each of the optical sensor unit includes: a coherent light source, a Fiber Bragg Grating (FBG), a photo detector, and a transmitter; at least a computation unit configured to: detect a deformation of a plurality of sides, wherein the plurality of sides corresponds to (i) one hexagon structure or (ii) at least two hexagon structures; at least a memory to store the detected deformation of the plurality of sides; wherein the transmitter transmits information related to the detected deformation to the centralized unit. In an embodiment, the information is transmitted from the transmitter to centralized unit through at least one of (i) a wireless medium channel or (ii) a wired medium channel. In an embodiment, the deformation of the plurality of sides is determined based on a difference in frequency of incident light and reflected light by the Fiber Bragg Grating. In an embodiment, the centralized unit is configured to: receive, the transmitted information related to the detected deformation; generate, signatures of movement patterns of one or more parts of body of a subject in accordance with the detected deformation; compare, the generated signatures with stored signatures of the movement patterns of the one or more parts of body of the subject; determine, an error indicative of distortion in the movement patterns of the one or more parts of body of the subject in accordance with a difference between the generated signature and the stored signature. In an embodiment, the signature of a specific movement pattern is generated based on aggregation of information transmitted to the centralized unit. In an embodiment, the error indicative of distortion is used to quantify range of motion of the movement patterns of the one or more body parts of the subject. In an embodiment, the centralized unit is further configured to provide an alert when the error indicative of distortion exceeds a pre-defined threshold, wherein the alert is displayed in an electronic device.

In yet another aspect, one or more non-transitory computer readable mediums for identifying distortion in movements and quantifying range of motion using sensor based wearable fabric design are provided. The one or more non-transitory computer readable mediums comprising one or more instructions which when executed by one or more hardware processors cause detecting deformation of a plurality of sides in a wearable fabric worn by the subject. In an embodiment, the deformation of the plurality of sides is determined based on a difference in frequency of incident light and reflected light by a Fiber Bragg Grating. In an embodiment, the instructions may further cause generating signatures of movement patterns of one or more parts of body of the subject in accordance with the detected deformation; comparing, the generated signatures with stored signatures of the movement patterns of the one or more parts of body of the subject; determining, an error indicative of distortion in the movement patterns of the one or more parts of body of the subject in accordance with a difference between the generated signatures and the stored signatures. In an embodiment, the signature of a specific movement pattern is generated based on aggregation of information transmitted to a centralized unit. In an embodiment, the information is transmitted from the transmitter to centralized unit through at least one of (i) a wireless medium channel or (ii) a wired medium channel. In an embodiment, the error indicative of distortion is used to quantify range of motion of the movement patterns of the one or more body parts of the subject. In an embodiment, the centralized unit provides an alert when the error indicative of distortion exceeds a pre-defined threshold, wherein the alert is displayed in an electronic device.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 7A through 7L illustrate different possible ways of deformation in sides of hexagon structures comprised in the sensor based wearable fabric design in accordance with some embodiments of the present disclosure.

FIGS. 8A through 8F show illustrative examples of movement patterns of the subject in accordance with some embodiments of the present disclosure.

Figure 1:
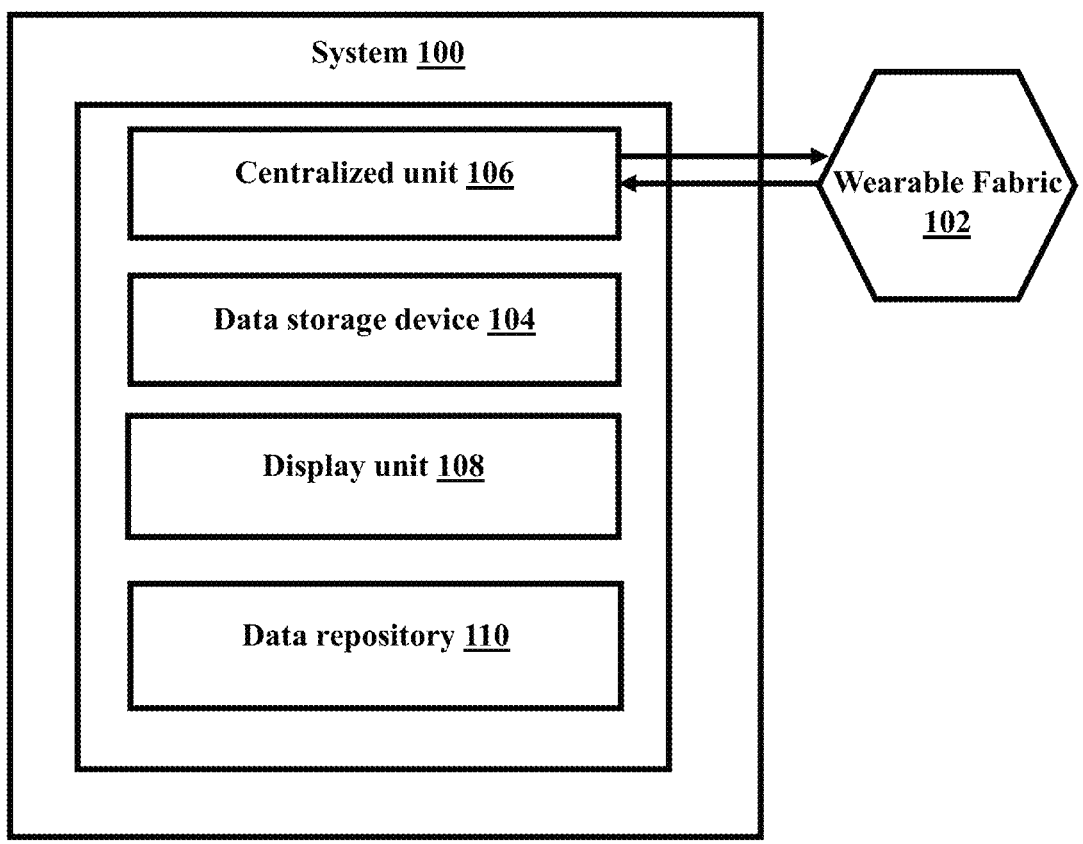
FIG. 1 illustrates an exemplary system having a wearable fabric for identifying distortion in movements and quantifying range of motion according to some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provide a sensor based wearable fabric design for identifying distortion in movements and quantifying range of motion. The typical interpretation of results obtained from conventional wearable fabric-based systems and methods has been modified to solve a problem of quantifying multi-axis complex range of motion. The range of motion is an essential part of clinical examination and is routinely used as a measure of function. For example, in case of joints, the range of motion, pain associated with the range of motion as well as the associated symptoms of distortion (e.g., crepitus and stiffness) are essential parts of the clinical examination of joints. A joint is a region of articulation between two bones. Human joints may have a complex range of motion and that can be dependent on a plurality of variables such as bone geometry, ligamentous and muscle anatomy and location.

However, most of the human joints have fundamental range of motion. For example, knee and elbow and the joints of the fingers (interphalangeal) with exception of thumb move in one axis only. In the knee joint, a round on flat articulation of tibia on femur is constrained by ligamentous attachments, to produce a predominantly uniaxial motion in flexion and extension. This seemingly uni-axial motion is also accompanied by rotations at end of the extension guided by the bony anatomy and ligamentous attachments. Therefore, the flexion-extension movement of the knee is a considered as a complex movement. However, there are joints which have more than a single axis of motion. For example shoulder, hip, and spine which are a series of joints linked together. It is difficult to measure the range of motion of the hip in a posture such as sitting cross legged which needs movements like abduction, external rotation and the flexion using conventional systems. Further, the range of motion of the shoulder, hip, and spine is non-planar, exists in all three fundamental body axes and, does not have a single or fixed axis of rotation. Further, pain and deformities might distort the axis to larger extent. In other words, the shoulder is a joint which is less constrained and has a multi axial range of motion in the planes of the flexion-extension, abduction-adduction, internal and external rotation as well as combined movements like circumduction.

Conventional systems and methods fail to provide accurate multi-axis complex range of motion measurements for clinical use. The proposed method and system provide a sensor based wearable fabric design for identifying distortion in movements and quantifying range of motion by using fiber optic grating technology. The wearable fabric is designed as a plurality of honey-comb structures comprising a plurality of adjacently placed hexagon structures with an optical sensor unit placed on each side of the hexagon structures. The optical sensor unit comprises a coherent light source, a Fiber Bragg Grating (FBG), a photo detector, and a transmitter 208. The present disclosure exploits property of the FBG to cause frequency shift in a received light signal and a transmitted light signal which is further used to identify distortion in movement patterns of a subject. The identified distortion is further used to quantify range of motion of the movement patterns of the subject.

Referring now to the drawings, and more particularly to FIGS. 1 through 9F, where similar reference characters denote corresponding features consistently throughout the figures, there are shown preferred embodiments and these embodiments are described in the context of the following exemplary system and/or method.

FIG. 1 illustrates a functional block diagram of a system 100 having a wearable fabric 102 for identifying distortion in movements and quantifying range of motion according to some embodiments of the present disclosure. The system 100 includes or is otherwise in communication with one or more hardware processors such as a centralized unit 106, a wearable fabric 102, a display unit 108, one or more data storage devices 104 operatively coupled to the centralized unit 106, and a data repository 110. The centralized unit 106, one or more components of the wearable fabric 102, the display unit 108, and the one or more data storage devices 104, may be coupled by a system bus (not shown in FIG. 1).

Figure 2:
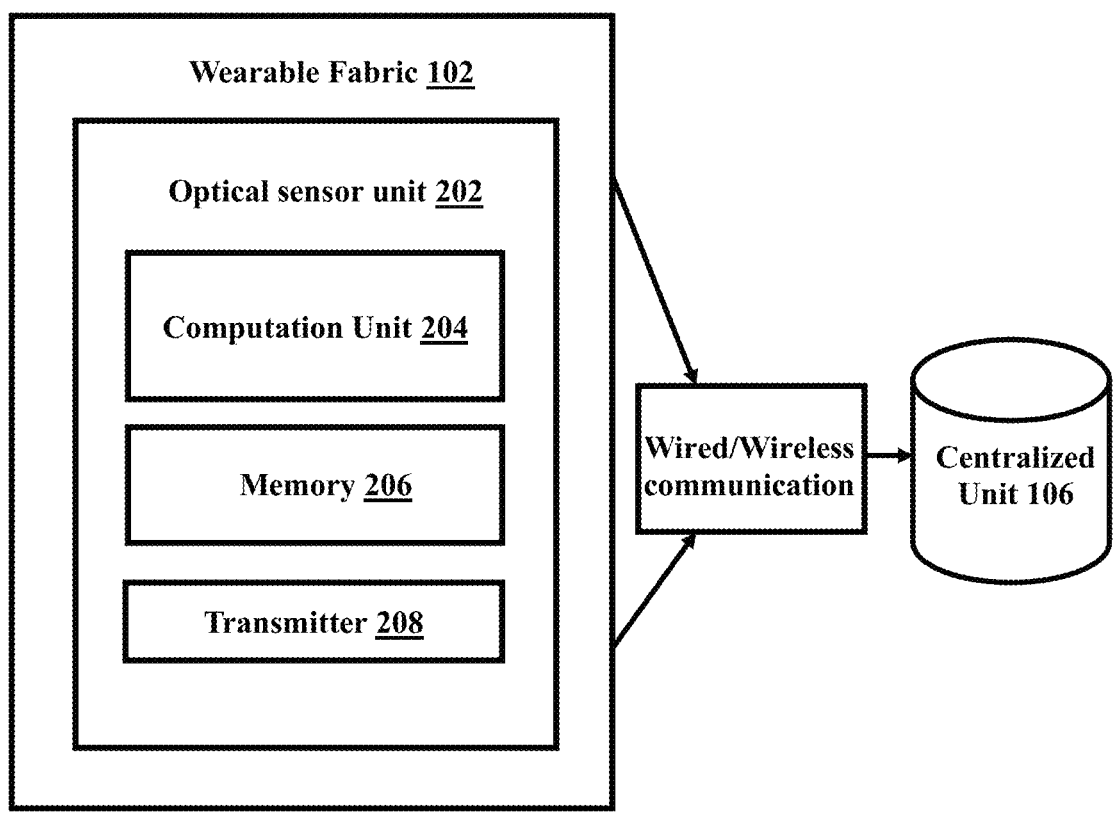
FIG. 2 is a functional block diagram of the wearable fabric of FIG. 1 for identifying distortion in movements and quantifying range of motion according to some embodiments of the present disclosure.
Figure 3:
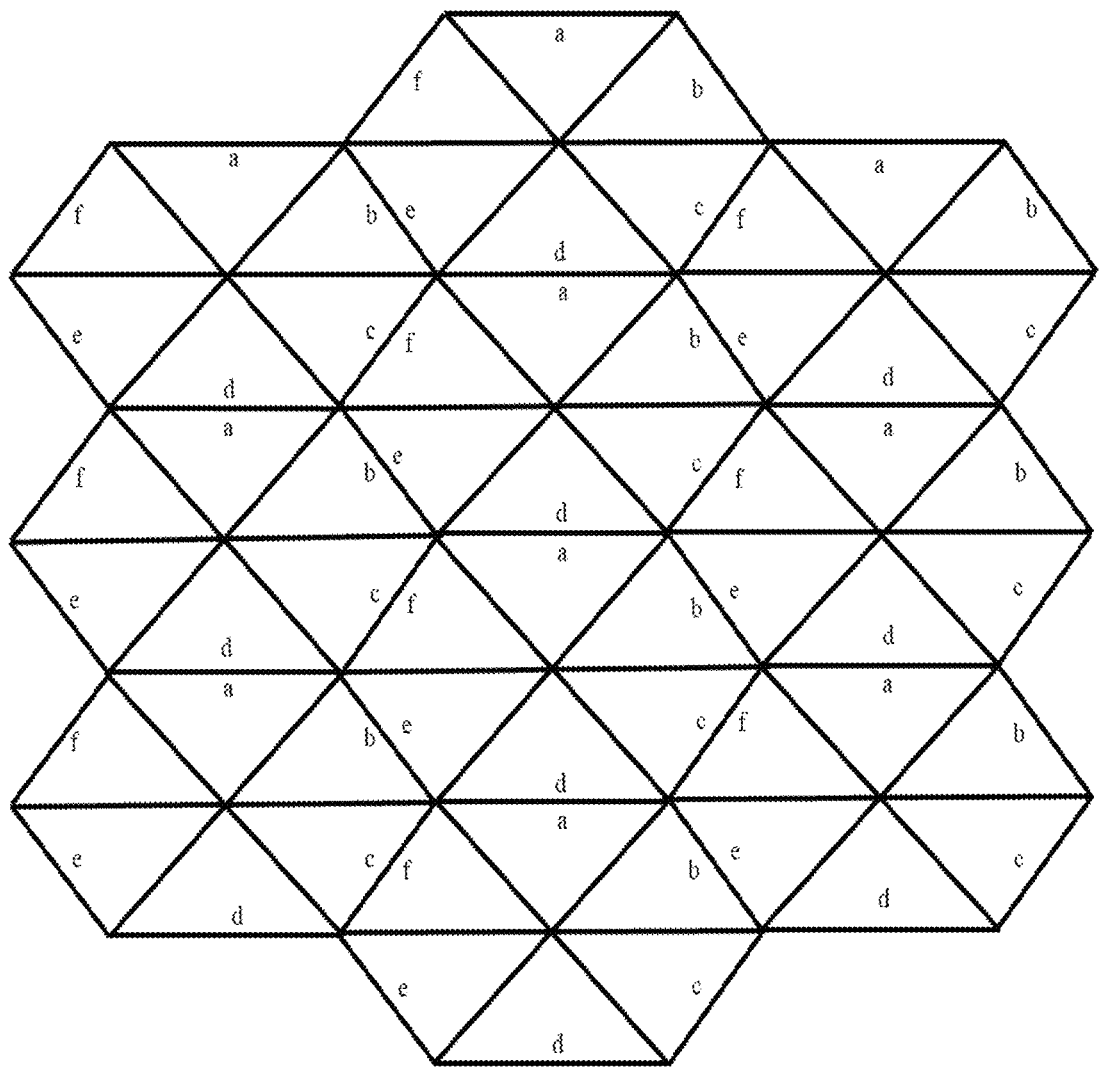
FIG. 3 is a schematic planar view of the sensor based wearable fabric design for identifying distortion in movements and quantifying range of motion in accordance with some embodiments of the present disclosure.

FIG. 2 is a functional block diagram of the wearable fabric 102 of FIG. 1 for identifying distortion in movements and quantifying range of motion according to some embodiments of the present disclosure. The wearable fabric 102 comprises a plurality of honey-comb structures, wherein each of the honey-comb structure comprising a plurality of adjacently placed hexagon structures. Each hexagon structure of each honey-comb structure comprises a plurality of optical sensor units 202 with each optical sensor unit placed on each side of the hexagon structure, at least a computation unit 204, and at least a memory 206. FIG. 3 is a schematic planar view of the sensor based wearable fabric design for identifying distortion in movements and quantifying range of motion in accordance with some embodiments of the present disclosure. The wearable fabric 102 comprises a plurality of honey-comb structures and each honey-comb structure comprises a plurality of adjacently placed hexagon structures as shown in FIG. 3. As can be seen in FIG. 3, each side of each hexagon structure is represented by a, b, c, d, e, and f respectively. Each optical sensor unit from the plurality of optical sensor units 202 is placed on each side of hexagon structures comprised in the plurality of plurality of honey-comb structures. The diagonals of each of the hexagon structure shown in FIG. 3 are used to provide support to each hexagon structure of the wearable fabric 102 and may be made up of textile fibre strands such as cotton, lycra, and the like. In an embodiment, design of the wearable fabric 102 is analogous to hexagonal closed packing (HCP) structures of solid state lattices, which proves to have highest 3D space efficiency so this wearable fabric 102 can be extended to 3D structures. In an embodiment, planar lattice structure of the wearable fabric 102 is also similar to that of graphite molecule which makes it a porous, breathable, better form fitting and comfortable garment.

The computation unit 204 of the wearable fabric 102 is configured to detect a deformation of a plurality of sides, wherein the plurality of sides corresponds to (i) one hexagon structure or (ii) at least two hexagon structures. In an embodiment, the computation unit 204 can be implemented as a stand-alone unit within the wearable fabric 102 but separated from the optical sensor units 202. In the arrangement where the computation unit 204 is separated from the optical sensor units 202, there is a possibility that each hexagon structure may have only one computation unit or each honey-comb structure may have only one computation unit. In another embodiment, the computation unit 204 may be a part of optical sensor units 202 placed on each side of the hexagon structures. In such cases, each side of each hexagon structure may have a computation unit.

Figure 4:
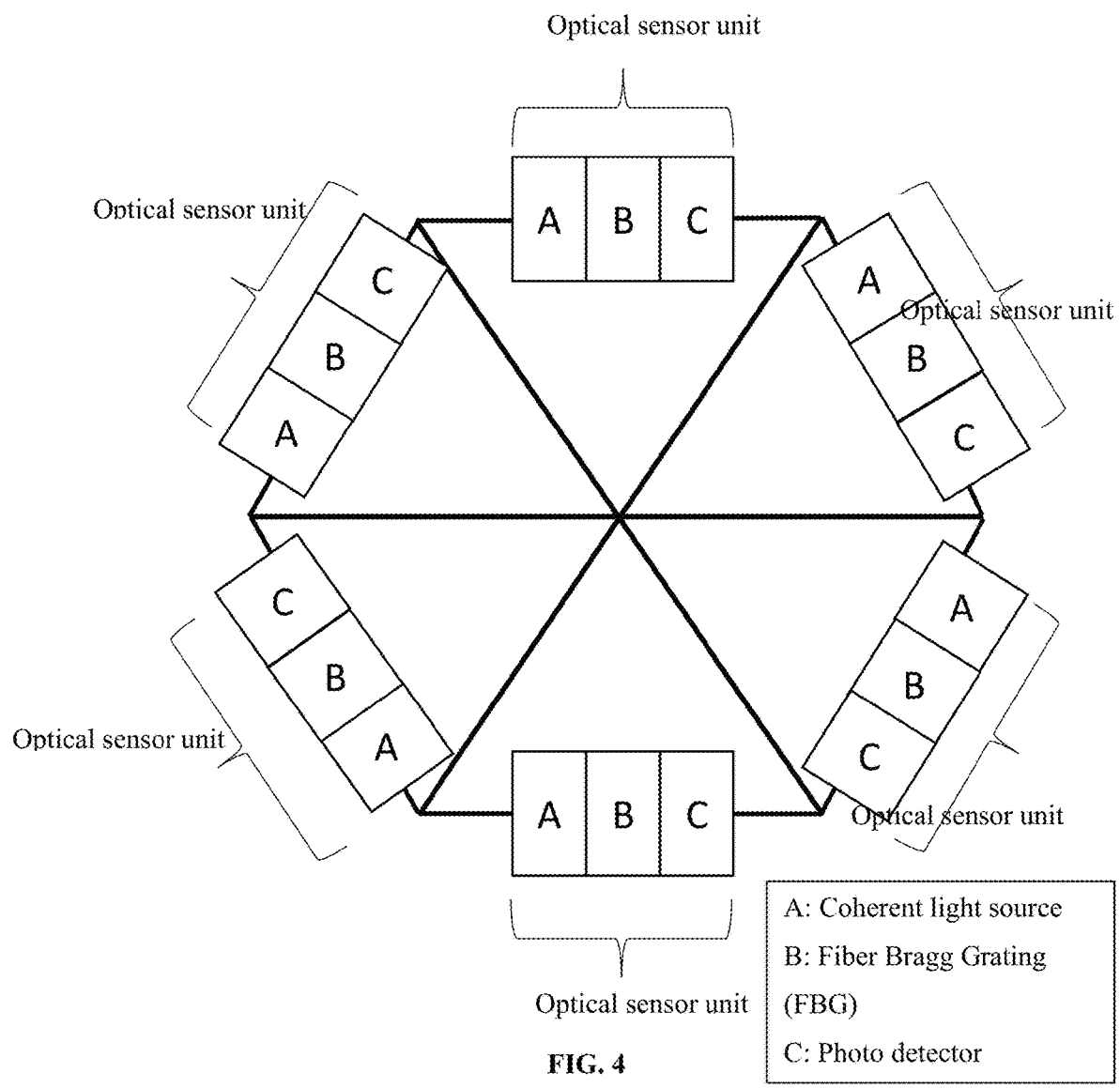
FIG. 4 illustrates a single knit element of the sensor based wearable fabric design for identifying distortion in movements and quantifying range of motion in accordance with some embodiments of the present disclosure.

In an embodiment, components of optical sensor unit 202 can be incorporated into woven fabrics. FIG. 4 illustrates a single knit element of the sensor based wearable fabric design for identifying distortion in movements and quantifying range of motion in accordance with some embodiments of the present disclosure. As can be seen from FIG. 4, the optical sensor units are placed on each side of the hexagon structures. The optical sensor unit 202 may include but not limited to a coherent light source, a Fiber Bragg Grating (FBG), a photo detector, and a transmitter (not shown in FIG. 4). In an embodiment, the coherent light source provides an input light signal of narrow wavelength (say 5-10 nanometer). The coherent light source may include but not limited to sun, candle, lamp, laser, bulb, super luminescent diode (SLD), and the like. The Fiber Bragg Grating (FBG) is a splitter which reflect a part of light input signal provided by the coherent light source and a difference of the input light signal incident on the FBG and reflected light signal by the FBG is determined and the difference is further transmitted to a photo detector. The photo detector is used to detect intensity of the light signal transmitted by the FBG. In an embodiment, intensity of detected light signal is a function of rotation of each of the optical sensor unit 202. In another embodiment, rotation experienced by each of the optical sensor unit 202 as a result of movement of one or more body parts of a subject is measured based on the percentage of detected light signal. The photo detector may include but not limited to photo diodes, photo transmitters, and the like. The transmitter 208 comprised in each of the optical sensor unit 202 transmits information related to the detected deformation of the plurality of sides of each of the hexagon structure to the centralized unit 106. In an embodiment, each optical sensor unit 202 is assigned a unique id represented as 32 hexadecimal (base-16) digits, such as '123e4567-e89b-12d3-a456-426655440000'.

The memory 206 of the wearable fabric 102 stores the detected deformation of the plurality of sides of each of the hexagon structure. In an embodiment, the memory 206 can be implemented as a stand-alone unit within the wearable fabric 102 separated from the optical sensor units 202. In the arrangement where the memory 206 is separated from the optical sensor units 202, there is a possibility that each hexagon structure may have only one memory or each honey-comb structure may have only one memory. In another embodiment, the memory 206 may be a part of optical sensor units 202 placed on each side of the hexagon structures. In such cases, each side of each hexagon structure may have a memory.

The computation unit 204 of the wearable fabric 102 and the centralized unit 106 of the system 100 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the centralized unit 106 is configured to fetch and execute computer-readable instructions stored in the one or more data storage devices 104. The centralized unit 106 may include routines, programs, objects, components, data structures, and so on, which perform particular tasks or implement particular abstract data types.

In an embodiment, the centralized unit 106 may be implemented as stand-alone unit separated from the wearable fabric 102. In another embodiment, the centralized unit 106 may be an integral part of the wearable fabric 102. In arrangements where the centralized unit 106 is separated from the wearable fabric 102, the centralized unit 106 may communicate with wearable fabric 102 through a wired or wireless communications medium. Wired communication mediums may include but not limited to Ethernet, serial, analog wires, universal serial bus (USB), and inter-IC bus (I2C). Wireless communications mediums may be implemented using wireless local area network protocols, protocols for other short-range wireless communication links. In an embodiment, the centralized unit 106 can be implemented in a variety of computing systems, such as laptop computers, notebooks, hand-held devices, edge devices, on-board devices, workstations, mainframe computers, servers, a network cloud and the like.

The memory 206 comprised in the wearable fabric 102 and the one or more data storage devices 104 of the system 100 may include any computer-readable medium known in the art including, for example, volatile memory, such as static random access memory (SRAM) and dynamic random access memory (DRAM), and/or non-volatile memory, such as read-only memory (ROM), erasable programmable ROM, flash memories, hard disks, optical disks, and magnetic tapes.

The data repository 110, amongst other things, includes a system database and other data. The other data may include data generated as a result of the execution of the centralized unit 106 and the computation unit 204 involved in techniques that are described herein. The system database stores data processed, received, and generated by centralized unit 106 and the computation unit 204 which includes data received from the optical sensor units 202, information transmitted to the centralized unit 106, deformation detected by the computation unit 204, signature of movement patterns and corresponding output which are generated as a result of the execution of the centralized unit 106 and the computation unit 204.

The display unit 108 of the wearable fabric 102 may include an electronic device such as a television, computer, laptop, portable devices like a wrist watch device, a pendant device, a cellphone, a media player, a gaming device, a navigation device, and health care equipment or other electronic equipment. In an embodiment, the display unit 108 may be used to analyze or monitor condition of a patient and provide an alert to the patient by displaying one or more parameters related to movement of one or more body parts of a subject. For example, in case of a person undergoing orthopedic surgery, intensity of pain can be determined by the wearable fabric 102 based on identified distortion in movement of one or more body parts of the subject. This detail can be sent to the display unit 108 to alert the patient. In a non-limiting example embodiment, the display unit 108 can be used in a gym for determining fitness condition of the subject under consideration and providing an alert to the subject regarding one or more fitness parameters. For example, the display unit 108 may provide alert regarding type of exercises which should not be performed by the subject due to distortion or likelihood of distortion in movements of one or more body parts of the subject.

In an embodiment, the centralized unit 106 of the system 100 can be configured to identify distortion in movements and quantifying range of motion using sensor based wearable fabric design. Identification of distortion in movements and quantification of range of motion using sensor based wearable fabric design can be carried out by using methodology, described in conjunction with FIG. 5 and use case examples.

Figure 5:
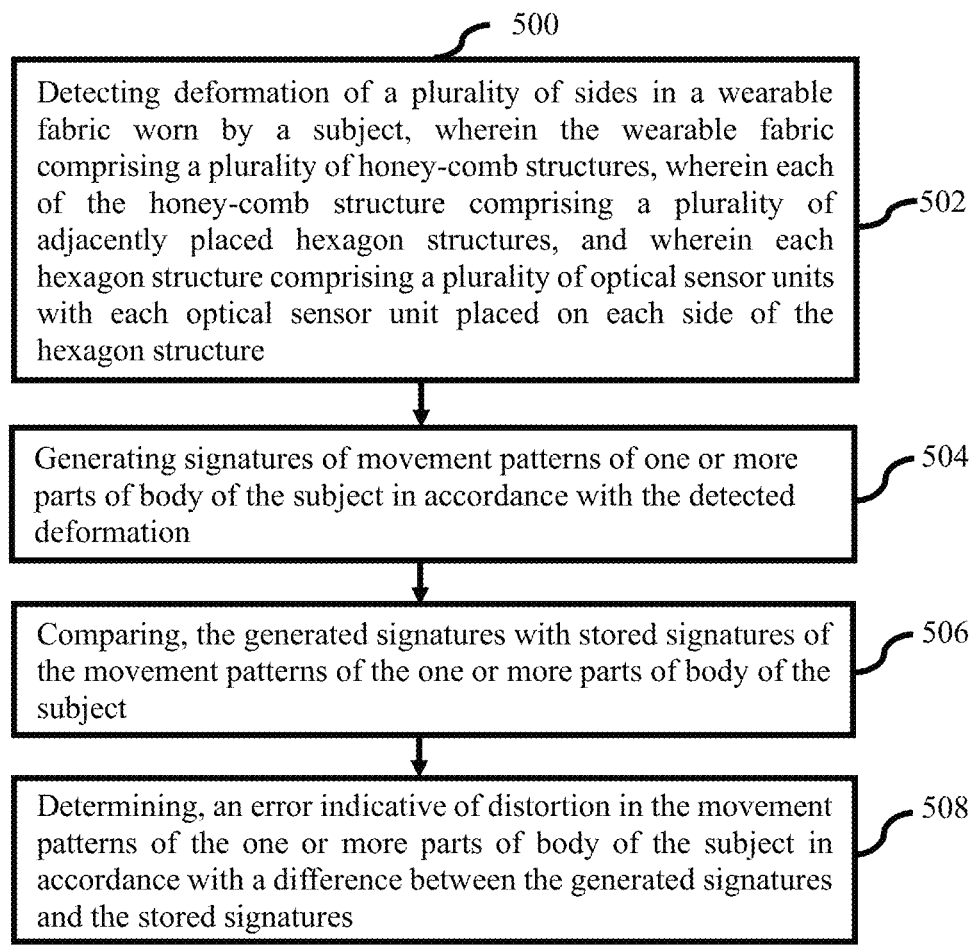
FIG. 5 is a flow diagram illustrating a method for identifying distortion in movement patterns of a subject in accordance with some embodiments of the present disclosure.

FIG. 5 is a flow diagram illustrating a method 500, implemented by the system 100 of FIG. 1 for identifying distortion in movement patterns of a subject, in accordance with some embodiments of the present disclosure.

In an embodiment, the system 100 comprises one or more data storage devices 104 or the memory 206 operatively coupled to the centralized unit 106 or the computation unit 204 and is configured to store instructions for execution of steps of the method 500 by the centralized unit 106 or the computation unit 204. The steps of the method 500 of the present disclosure will now be explained with reference to the components of the system 100 and the wearable fabric 102 as depicted in FIG. 1 and FIG. 2 and the steps of flow diagram as depicted in FIG. 5. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Referring to FIG. 5, at step 502, the computation unit 204 is configured to detect deformation of a plurality of sides in the wearable fabric 102 worn by the subject. As depicted in FIG. 2, the wearable fabric 102 comprises a plurality of honey-comb structure with each honey-comb comprising a plurality of adjacently placed hexagon structures. Here, each hexagon structure comprising a plurality of optical sensor units with each optical sensor unit placed on each side of the hexagon structure. In other words, each side of each hexagon structure is representative of optical sensor unit 202. Thus, deformation of a side represents rotation of an optical sensor unit by an angle. In an embodiment, the rotation of optical sensor unit is caused due to abnormalities in the movement patterns of one or more body parts of a subject. In an embodiment, said abnormalities may be generated as a result of a surgery, pain, excessive exercise, and the like. As shown in FIG. 4, the optical sensor unit comprises a coherent light source, a FBG grating and a photo detector. In an embodiment, the optical sensor unit can be implemented as interferometry fiber optic (FO) gyroscopes. The interferometry fiber optic (FO) gyroscopes are inertial sensors that yield highly accurate absolute position and rotation information by virtue of the principle of Sagnac interferometry wherein two counter-propagating waves experience a differential phase delay. This differential phase delay can be very small, so interferometric methods are used to detect (and quantify) it. This differential phase delay is directly proportional to change in rotation angle of the interferometry fiber optic (FO) gyroscopes. Thus, by considering the optical sensor units 202 to be functioning as interferometry fiber optic (FO) gyroscopes, change in angle of rotation of optical sensor units 202 can be determined. This change in the angle of rotation is hereby referred as angle of deformation of the side of the hexagon structure. In an embodiment, principle of Sagnac interferometry is explained with the help of FIG. 6.

Figure 6:
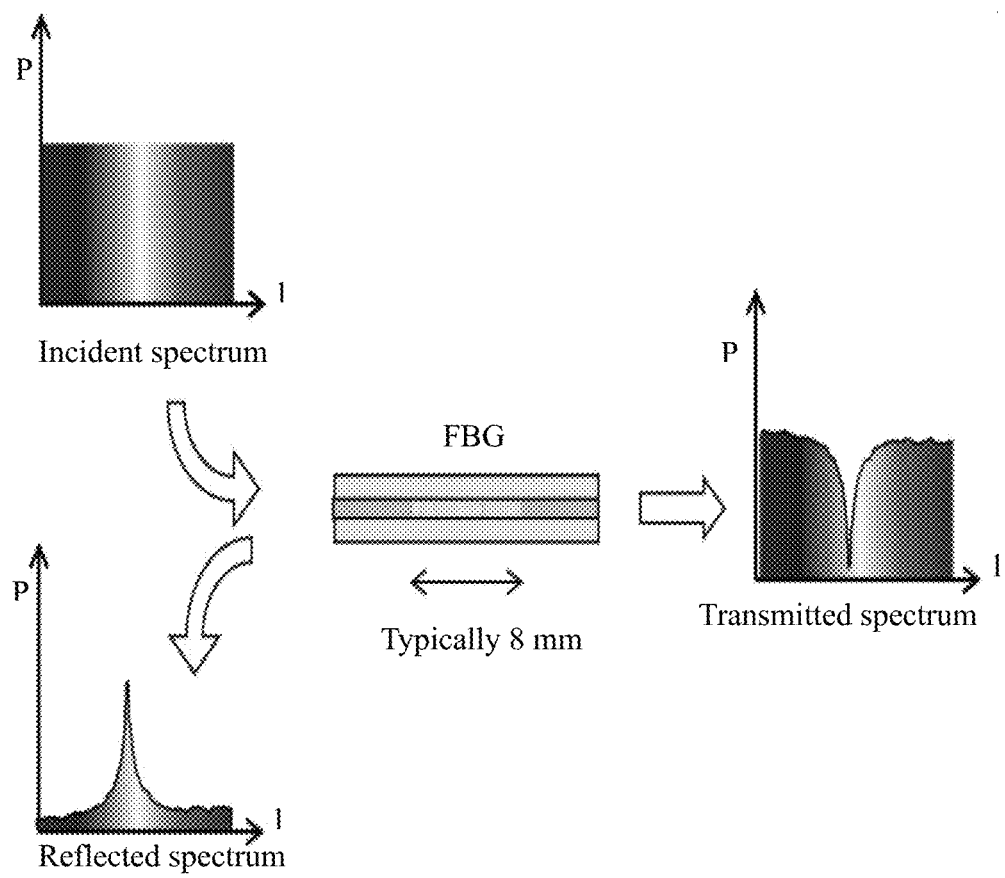
FIG. 6 is a diagram illustrating working of Fibre Bragg Grating (FBG) for identifying distortion in movements and quantifying range of motion in accordance with some embodiments of the present disclosure.

FIG. 6 is a diagram illustrating working of Fibre Bragg Grating (FBG) for identifying distortion in movements and quantifying range of motion in accordance with some embodiments of the present disclosure. As can be seen in FIG. 6, the FBG comprised in the optical sensor unit 202 receives a light signal from the coherent light source. The FBG is a device that is essentially built into a strand of optical fiber. The Fiber Bragg Gratings (FBGs) are made by laterally exposing core of a single-mode optical fiber to a periodic pattern of light signal received from an intense coherence light source (say laser light). The exposure produces a permanent increase in refractive index of the optical fiber's core, creating a fixed index modulation according to exposure pattern. This fixed index modulation is called a grating. In other words, the FBG has to contain alternating periods of high and low refractive index regions, like a grating. Essentially, if light of a finite bandwidth is sent into the FBG, a part of input spectrum, which corresponds to a Bragg reflection condition is reflected back and transmitted spectrum (which represents light detected at the output) contains all wavelengths minus those that were reflected back. At each periodic refraction change a small amount of light signal falling on the FBG is reflected. All the reflected light signals combine coherently to one large reflection at a particular wavelength when grating period is approximately half the received light signal's wavelength. This is referred to as the Bragg reflection condition, and the wavelength at which this reflection occurs is called Bragg wavelength. Light signals at wavelengths other than the Bragg wavelength, which are not phase matched, are essentially transparent. Therefore, received light signal propagates through the FBG with negligible attenuation or signal variation. Only those wavelengths that satisfy the Bragg reflection condition are affected and strongly back-reflected. The ability to accurately preset and maintain the grating wavelength is a fundamental feature and advantage of fiber Bragg gratings (FBGs). In an embodiment, central wavelength of reflected light signal component satisfies a Bragg relation: $\lambda_{Bragg}=n\nu$, wherein n depicts the index of refraction and v depicts period of index of refraction variation of the FBG. Further, parameters n and v are dependent on temperature and strain, so the wavelength of the reflected light component also changes as function of temperature and/or strain. This dependency allows determining the temperature or strain from the wavelength of the reflected light component. Thus, in the present disclosure, some part of the light signal received by the FBG from the coherent light source is reflected and remaining part of the received light signal is transmitted to the photo detector. Further, the photo detector determines intensity of the detected light which is used as a measure of rotation of the optical sensor unit 202. In an embodiment, deformation of the plurality of sides is determined based on a difference in frequency of received light signal and reflected light signal by the FBG. In another embodiment, the FBG is based on shift in frequency of incident light that falls on a fringe grating due to the change in the angle of rotation of the optical sensor units 202. If the original frequency due to interference between incident light source and the fringe pattern is f, which is pre-known by design, and the change in the angle of rotation of the optical sensor unit 202 by φ causes a shift to frequency f' as δf=f-f', then φ is provided as shown in equation (1) below:

$$\varphi = a\delta f + b \quad (1)$$

Here, a and b are coefficients learnt through a least square estimation method, performing experiments where φ is known. So $\|a\delta f + b - \varphi\|_{min}^2$ gives optimum values of a and b.

Figure 7A:
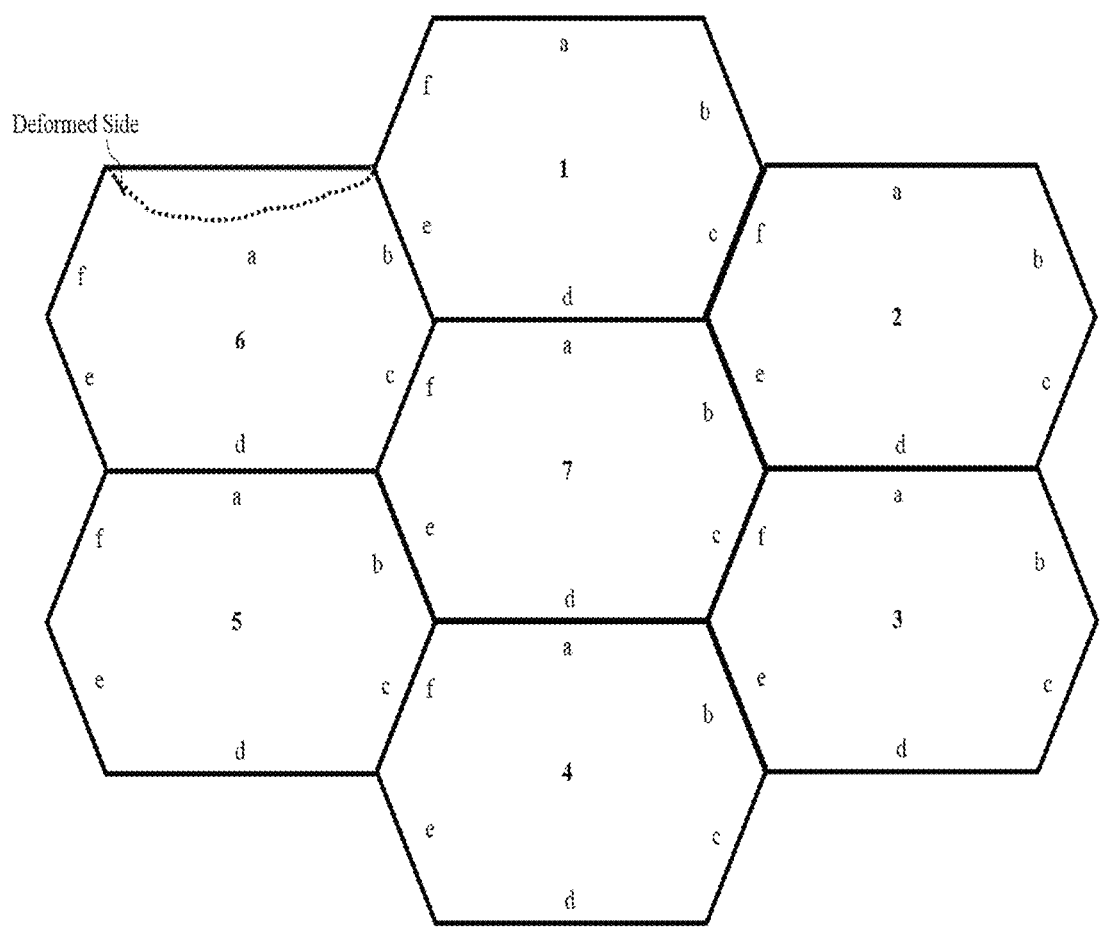
Figure 7B:
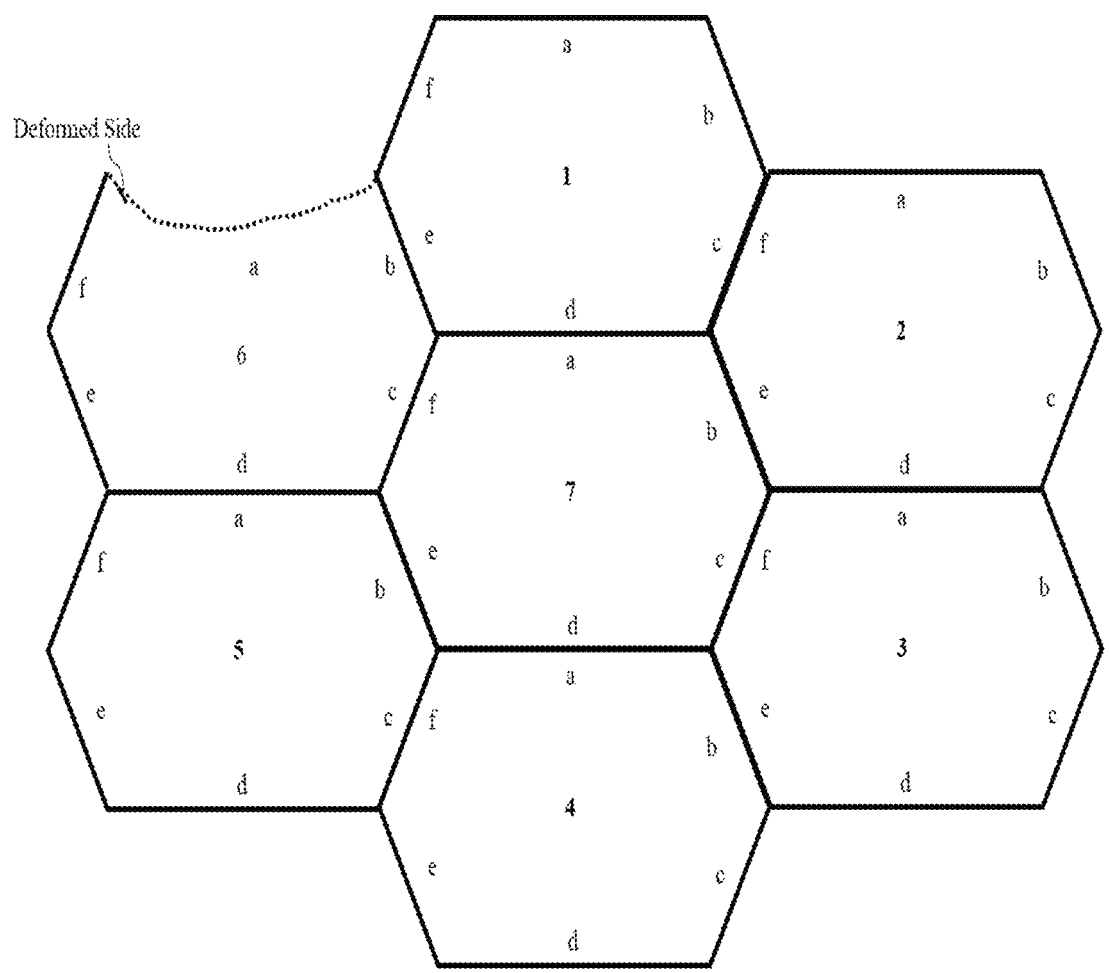
Figure 7C:
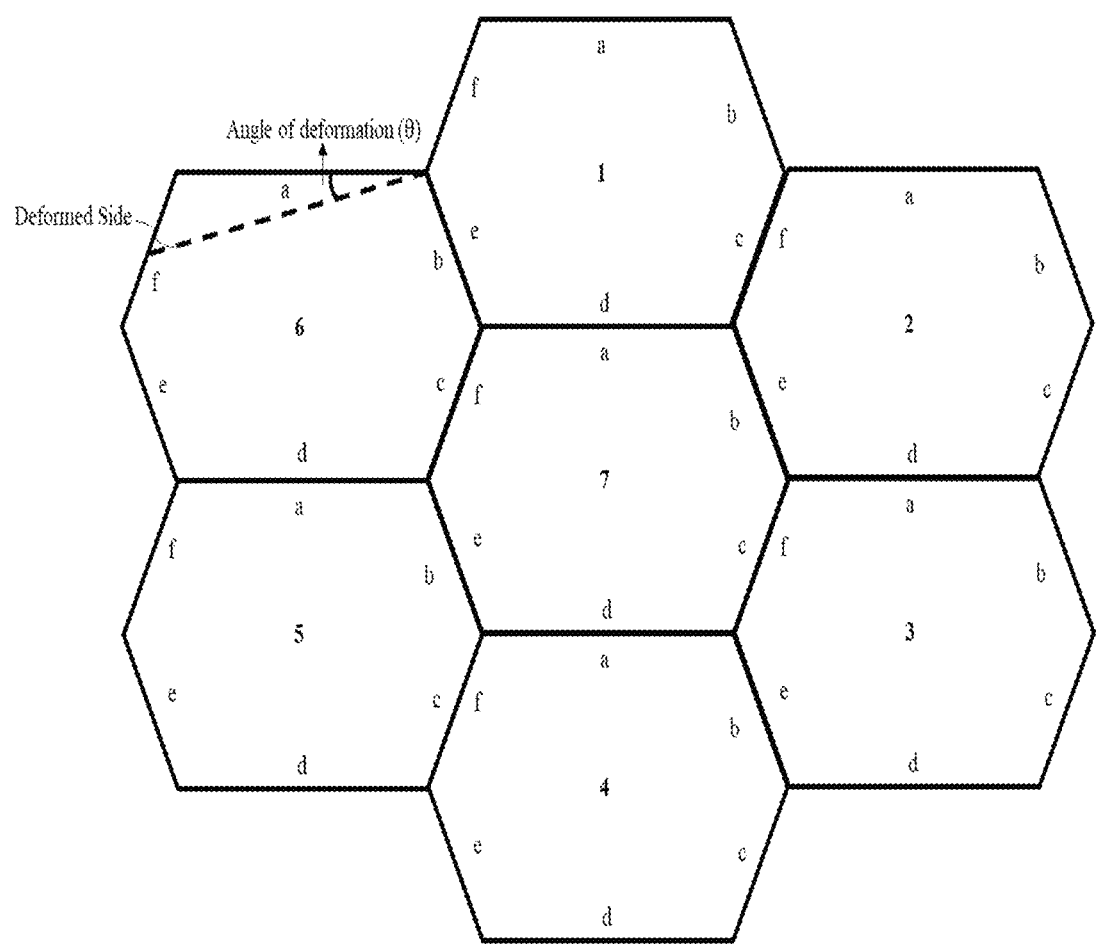
Figure 7B:
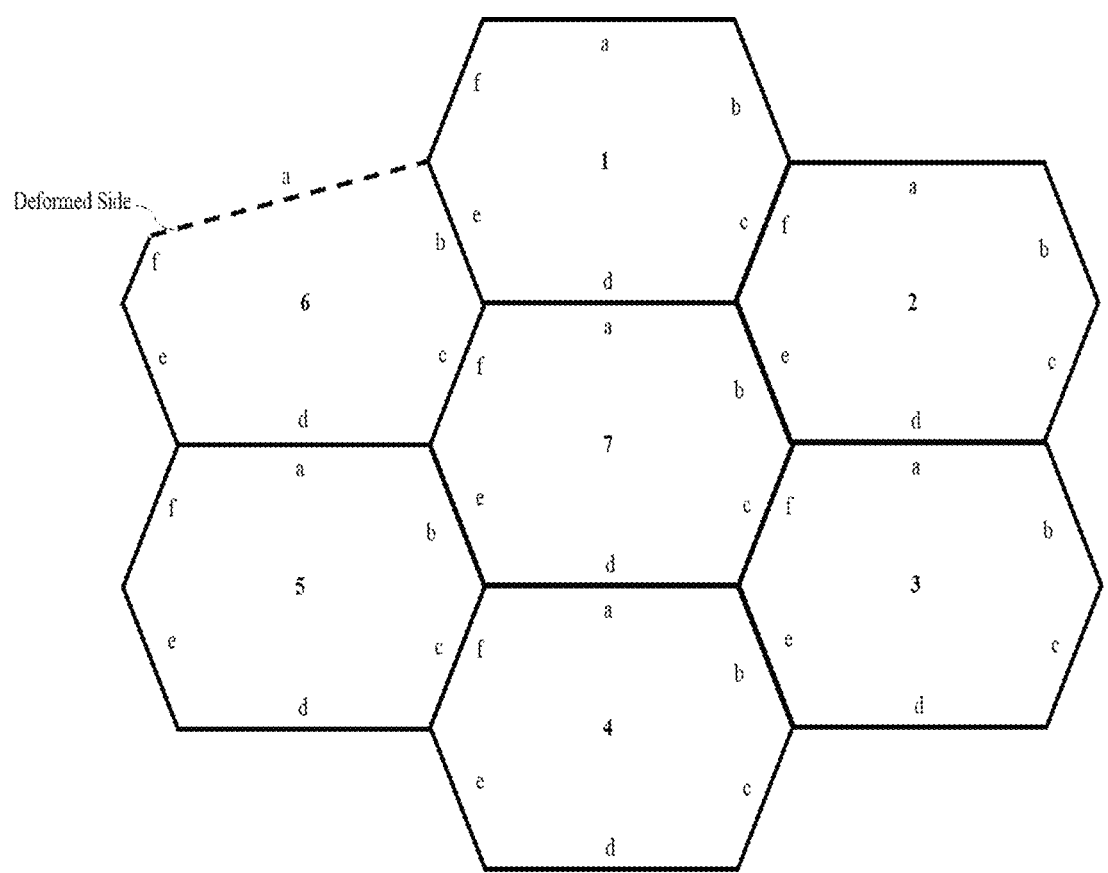

In an embodiment, the plurality of sides detected with deformation may correspond to (i) one hexagon structure or (ii) at least two hexagon structures. This can be explained with the help of FIGS. 7A through 7L. FIGS. 7A through 7L illustrate different possible ways of deformation in the sides of hexagon structures comprised in the sensor based wearable fabric design in accordance with some embodiments of the present disclosure. The deformation of side may have a uniform form (e.g. straight line) or non-uniform form (e.g., curved lines, spiral lines, and the like). In case of non-uniform deformation, the angle of deformation is determined based on the stress or strain, where said stress/strain are determined from the wavelength of the reflected light component by FBG. As can be seen in FIGS. 7A and 7B (Here, 7B is providing clear representation of deformed side shown in FIG. 7A), only one side (here side a) of one hexagon structure (hexagon 6) is deformed, wherein the deformation of side is non-uniform. Dotted line shown in FIGS. 7A and 7B represents deformed side. Similarly, in FIGS. 7C and 7D (Here, 7D is providing clear representation of deformed side shown in FIG. 7C), only one side (here side a) of one hexagon structure (hexagon 6) is deformed by an angle of deformation(θ), wherein the deformation of side is uniform. In an embodiment, the uniform deformation of sides may result in alteration in the length of adjacent side of the deformed side (e.g. length of side T of hexagon 6 is reduced in FIGS. 7C and 7D).

Figure 7E:
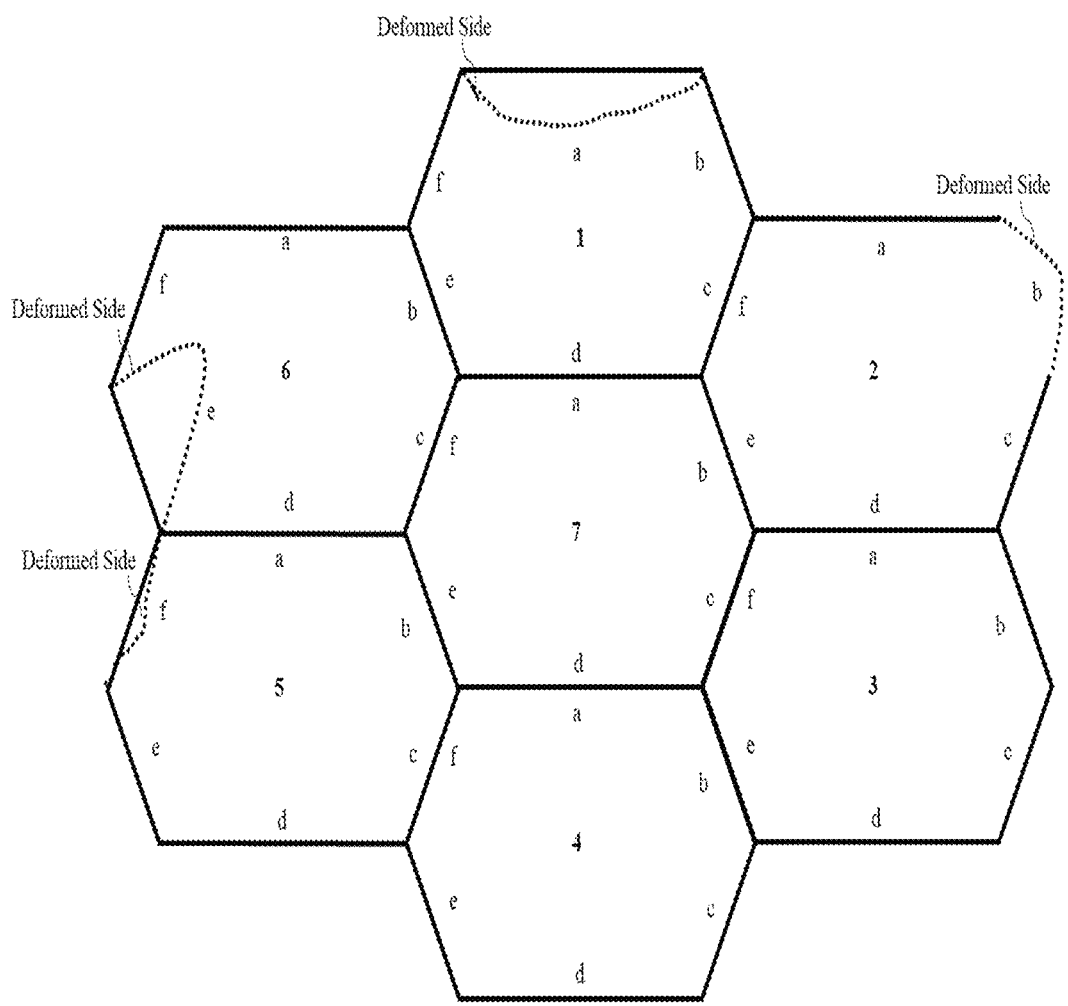
Figure 7F:
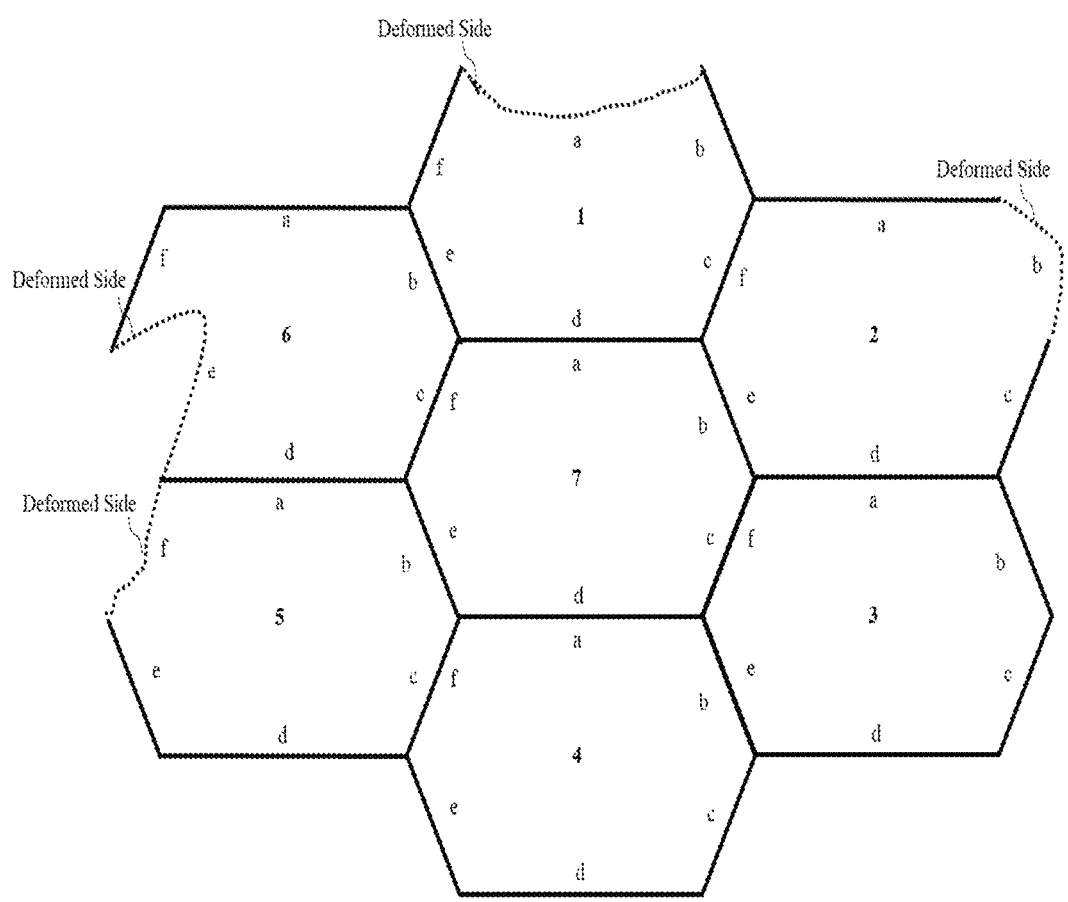
Figure 7G:
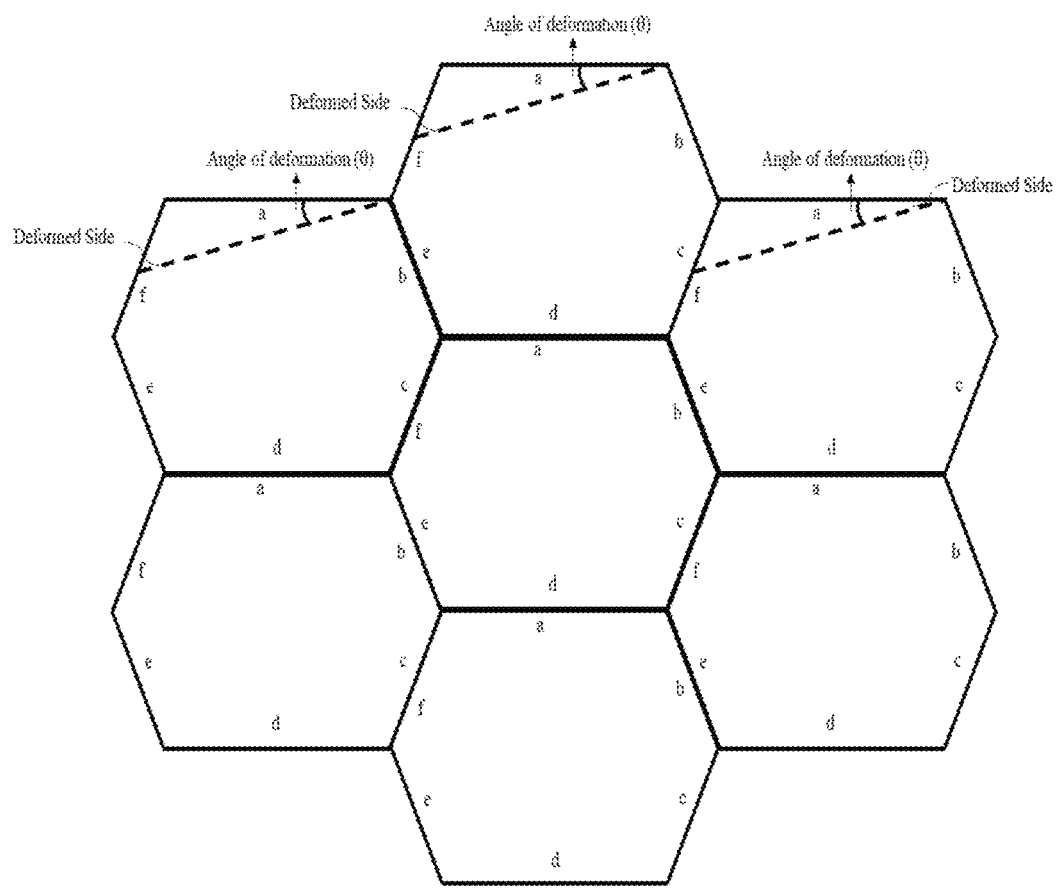
Figure 7H:
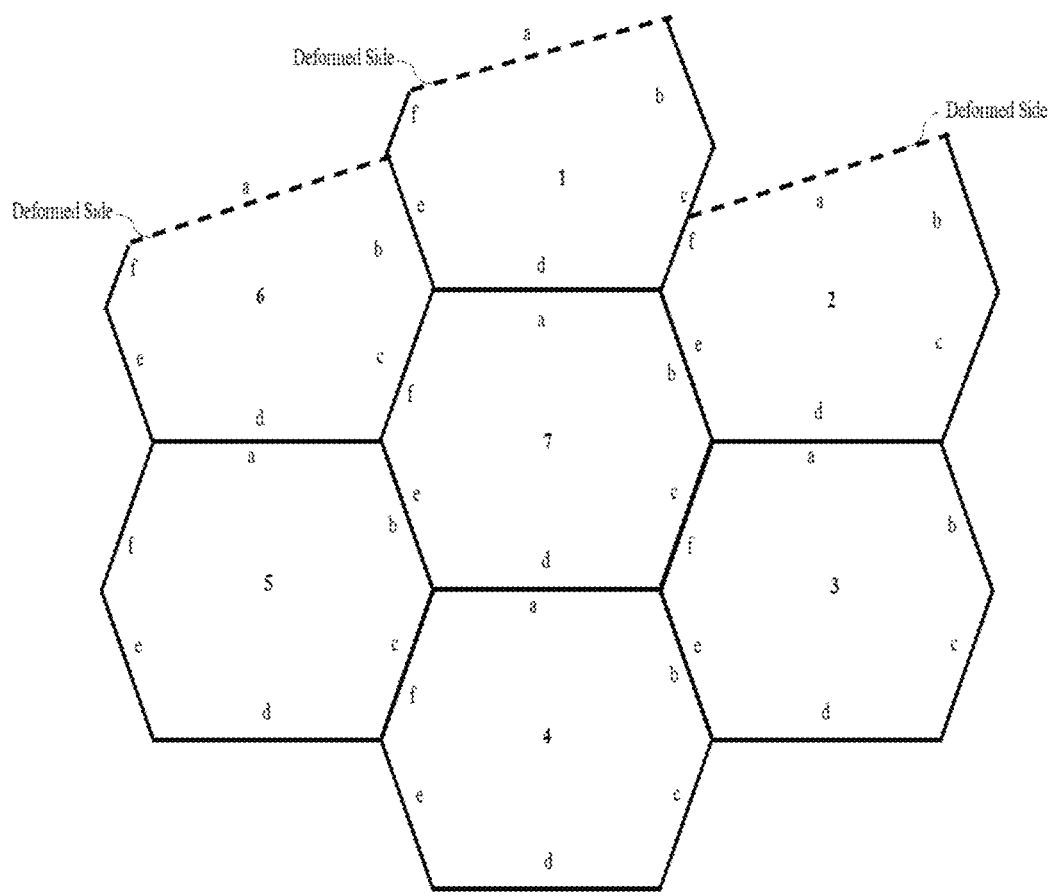
Figure 7I:
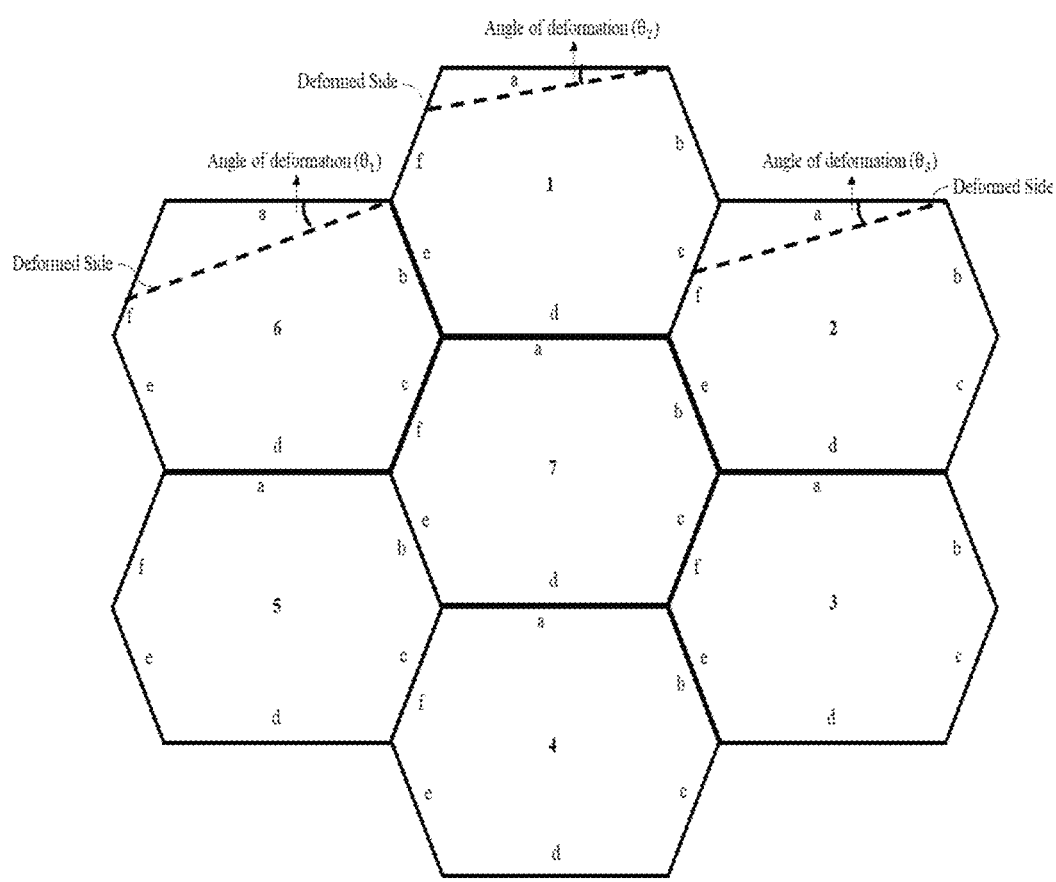
Figure 7J:
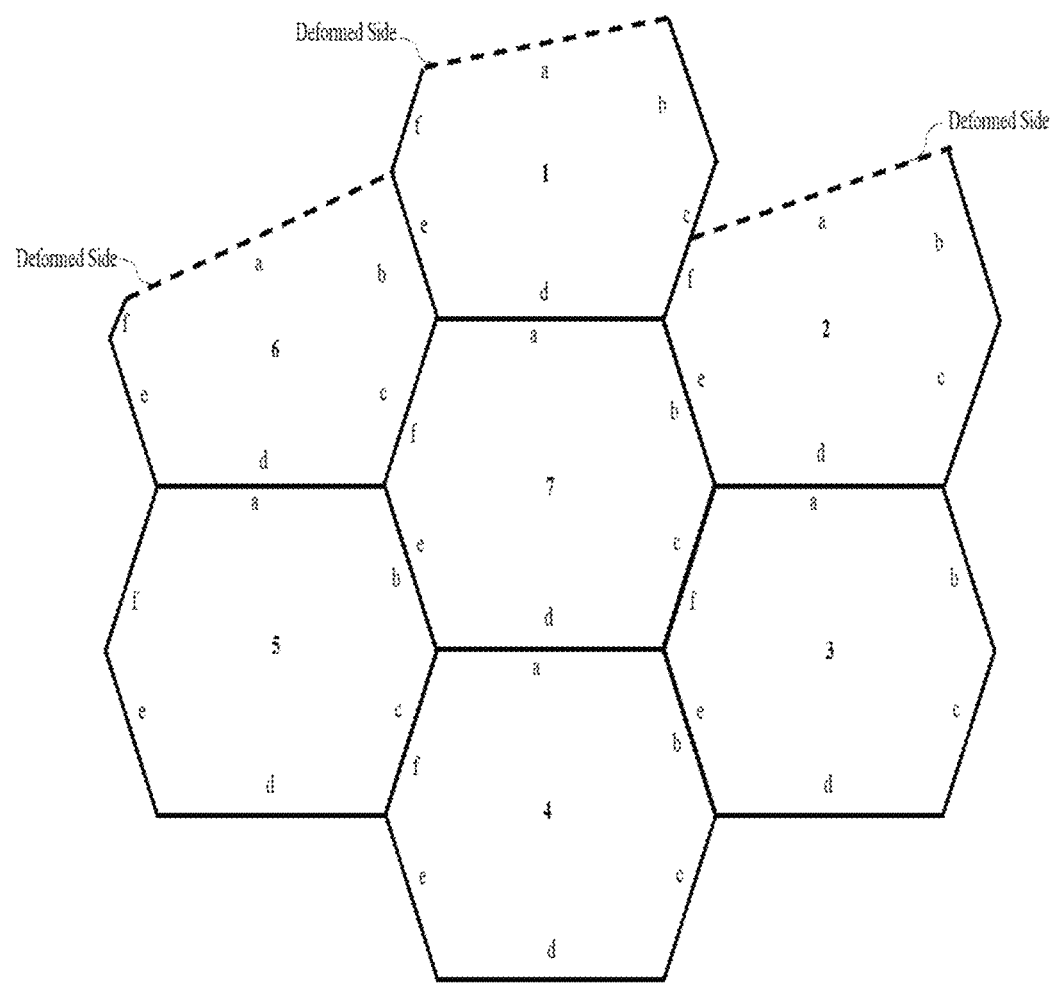
Figure 7K:
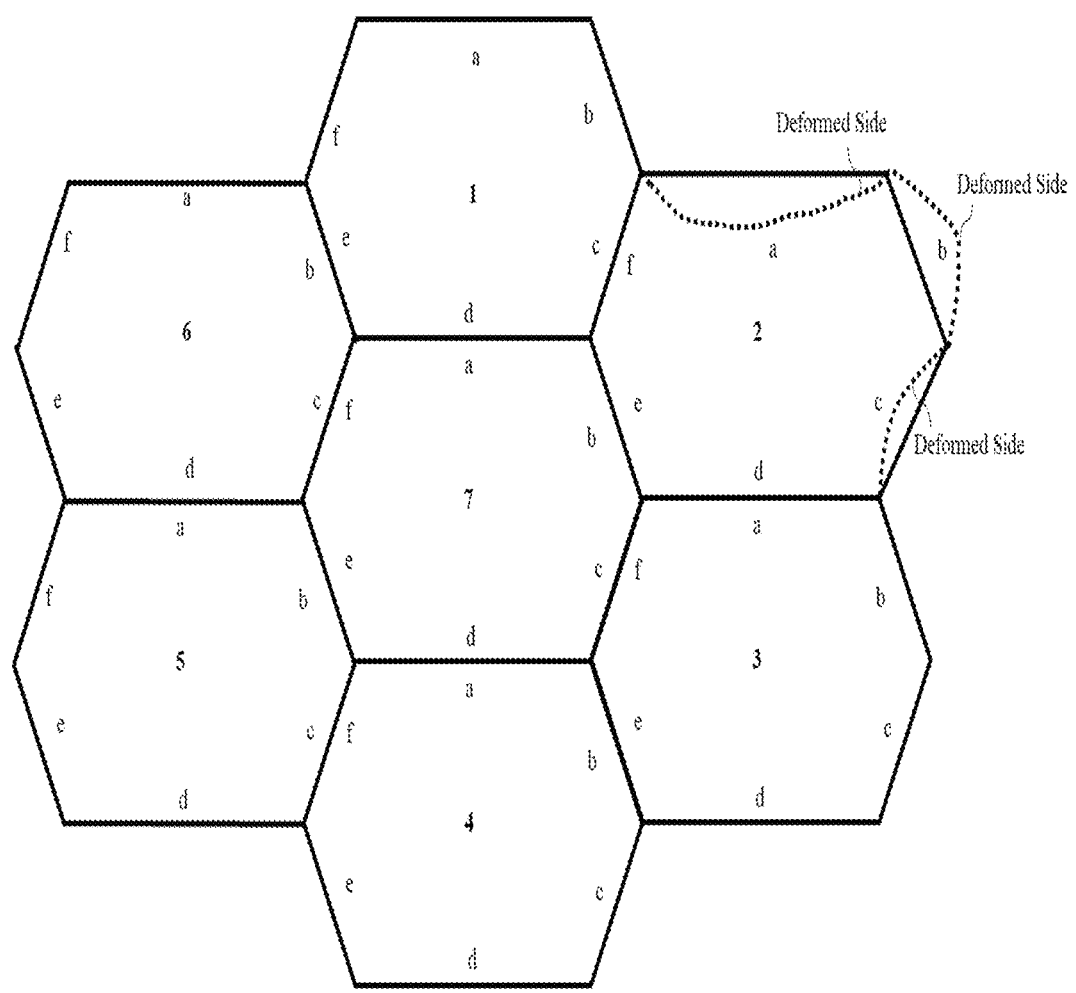
Figure 7L:
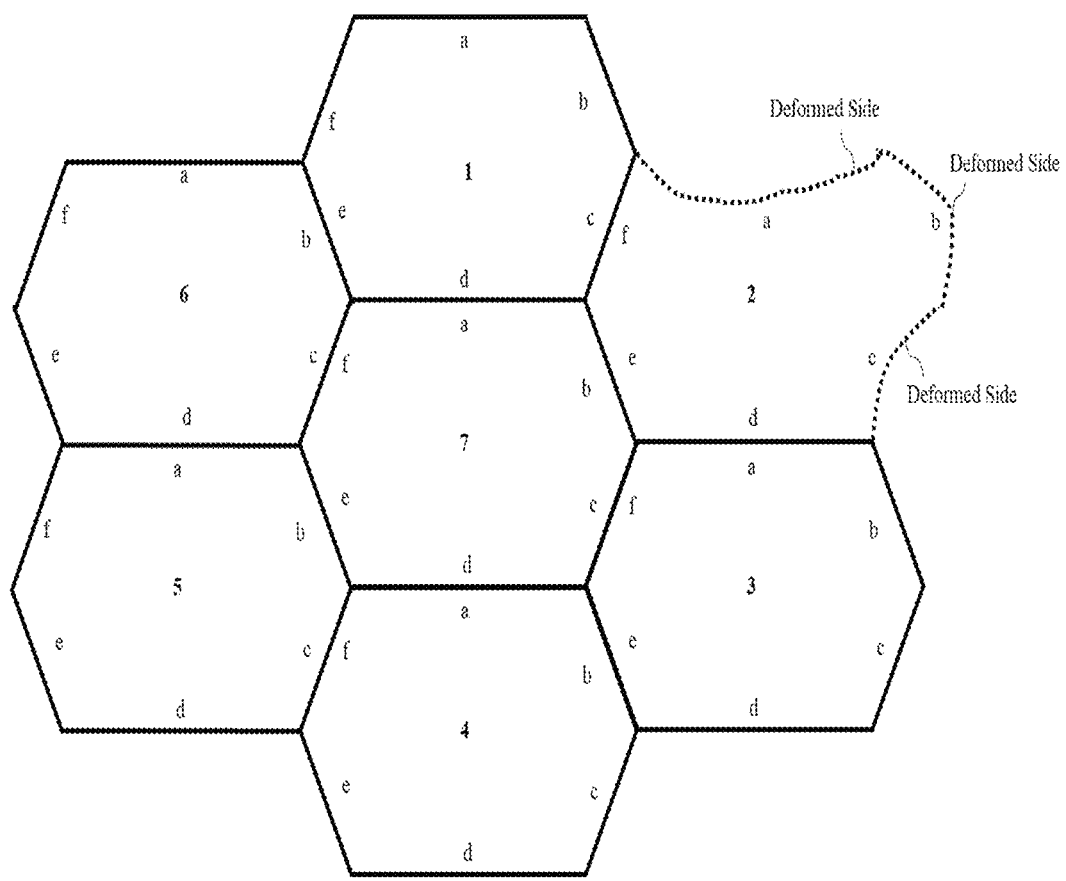
Figure 8C:
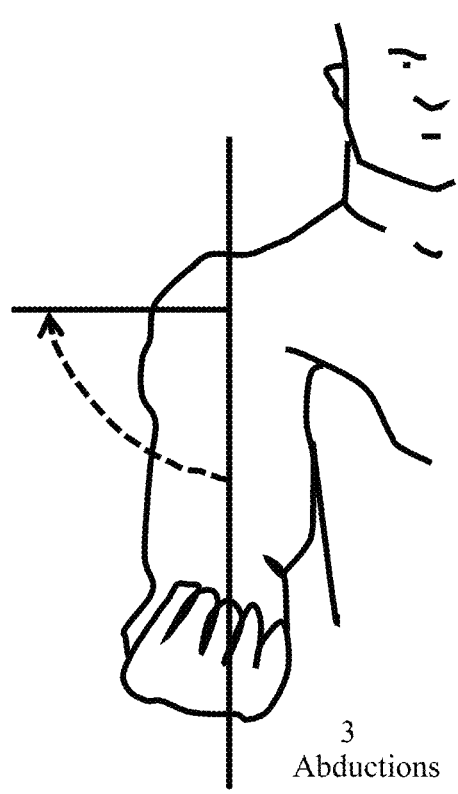
Figure 8D:
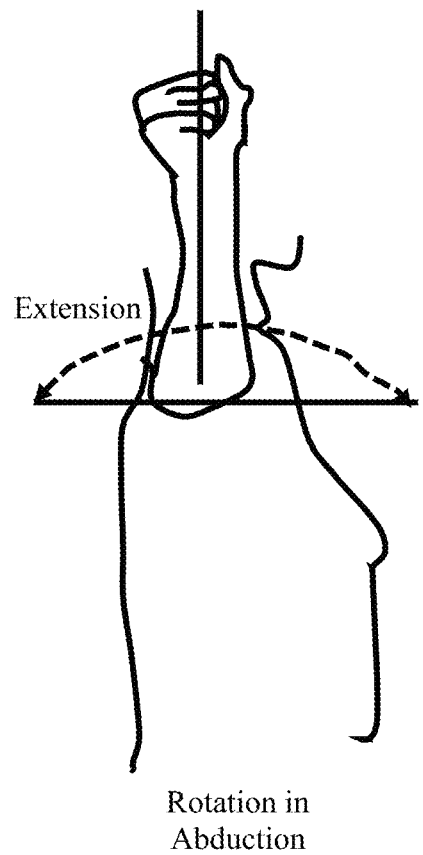
Figure 8E:
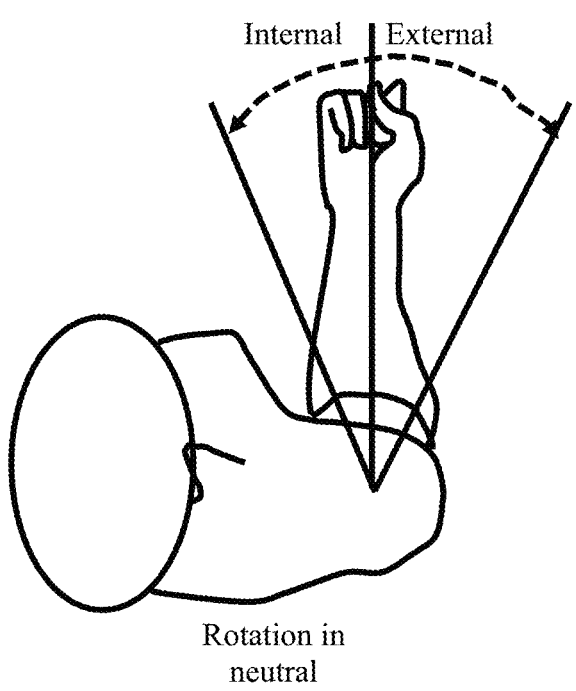
Figure 8F:
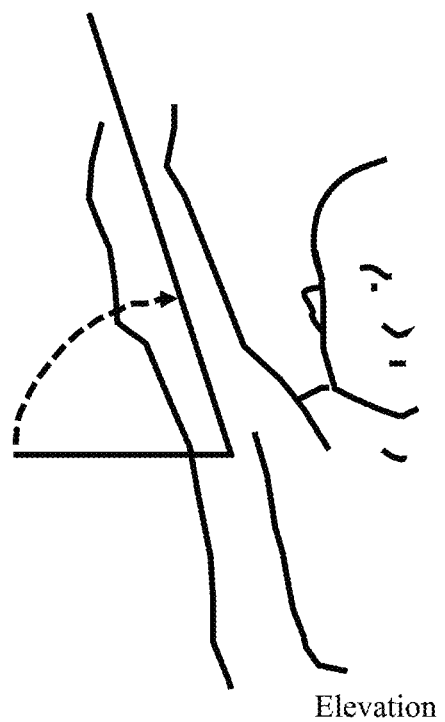

Further, there is possibility of deformation of one side of many hexagon structures or many sides of one hexagon structure. Also, the deformed side of one hexagon structure may be same as the deformed side of other hexagon structures or different. FIGS. 7E and 7F (Here, 7F is providing clear representation of deformed side shown in FIG. 7E) show non-uniform deformation of one side of many hexagon structures. As can be seen in FIGS. 7E and 7F, side 'a' of hexagon 1 is deformed. However, in hexagon 2, hexagon 5, and hexagon 6, the deformed sides are side 'b', side 'f', and side 'e' respectively instead of side 'a'. Similarly, FIGS. 7G and 7H (Here, 7H is providing clear representation of deformed side shown in FIG. 7G) show uniform deformation of one side of many hexagon structures. For example, as depicted in FIGS. 7G and 7H, same side 'a' of hexagon 1, hexagon 2, and hexagon 6 is deformed with same angle of deformation (θ). However, FIGS. 7I and 7J (Here, 7J is providing clear representation of deformed side shown in FIG. 7I) show uniform deformation of one side of many hexagon structures, wherein angle of deformation of deformed sides is different for different hexagons. As can be seen in FIGS. 7I and 7J, the same side 'a' of hexagon 1, hexagon 2, and hexagon 6 is deformed, but with different angle of deformations (say $\theta_2$, $\theta_3$, and $\theta_1$ respectively). Furthermore, FIG. 7K and FIG. 7L (Here, 7L is providing clear representation of deformed side shown in FIG. 7K) show deformation of many sides of one hexagon structure, wherein the deformation of sides is non-uniform. For example, as depicted in 7K and FIG. 7L, side 'a', side 'b', and side 'c' of hexagon 2 only are deformed.

In an embodiment, each optical sensor unit 202 comprised in the wearable fabric 102 is assigned a sensor ID. Each optical sensor unit 202 provides value of the angle of rotation by which it has gotten rotated along with the corresponding sensor ID. This information is saved in the memory 206 comprised in the wearable fabric 102 and transmitted by the transmitter 208 comprised in the optical sensor unit 202 to the centralized unit 106 using wired or wireless transmission.

Referring back to FIG. 5, at step 504, the centralized unit 106 is configured to generate signatures for movement patterns of one or more parts of body of the subject in accordance with the detected deformation. The centralized unit 106 aggregates the transmitted information related to the detected deformation of the plurality of sides to generate a signature of a specific movement pattern (alternatively referred as unified ROM signature). In an embodiment, there could be different movement patterns of one part of body of the subject. FIGS. 8A through 8F show illustrative examples of movement patterns of the subject in accordance with some embodiments of the present disclosure. As can be seen in FIGS. 8A through 8F, different movement patterns of human shoulder are provided. The movement patterns of human shoulder may include forward movements which includes but not limited to flexion, extension, neutral, abduction, rotation in abduction, rotation in neutral, elevation, and the like. Here, the range of motion of above-mentioned forward movements is determined based on direction of the range of motion which may vary from 0 degrees for neutral to 160 degrees for elevation. Further, signatures of flexion, extension, neutral, abduction, rotation in abduction, rotation in neutral, and elevation could be different for same body part (in this case, human shoulder).

Further, as depicted in step 504 of FIG. 5, the centralized unit 106 is configured to compare, the generated signatures with stored signatures of movement patterns of the one or more parts of body of the subject. In an embodiment, the generated signature of the specific movement pattern is used to construct a trajectory. As an example, it is assumed that for a specific movement pattern A, the stored signature is S. However, for a patient wearing the wearable fabric 102, the generated signature of same movement pattern A becomes S'. Further, using the generated signature S', a trajectory A' is constructed and a trajectory matching algorithm between A and A' is performed. In an embodiment, a method for trajectory matching involves making both trajectories piecewise linear using multi-layer perceptron (MLP) and then fit subsequent lines to calculate square of the errors on fitting. So, $$E = E_1 + E_2 \ldots + E_n \quad (2)$$

Where, $E_i = (L_i - L'_i)$ and $L_i = i^{th}$ line approximation from movement pattern, wherein line approximations are by the movement pattern A as provided in equation 3 below as:

$$\{L_1, L_2, \ldots L_n\} = \text{linearise}(A) \quad (3)$$

Here, L represents linear approximation of the trajectory and E represents error between actual and expected trajectory. L and E are measure of abnormality. In an embodiment, the step of comparing the generated signature with stored signatures of movement patterns of the one or more parts of body of the subject may involve a one to one mapping or one to many mapping. The one to one mapping refers to comparing the generated signatures of movement patterns of one body part to the stored signatures of same body part. For example, if a signature is generated for knee movement, then the generated signature must be mapped with the stored signature of knee movements only in case of one to one mapping. To achieve one to one mapping, a classification or categorization of movement patterns belonging to different body parts may be required. For example, all the movement patterns related to shoulder should be categorized as class 1, movement patterns related to knee as class 2, and the like. However, the one to many mapping refers to comparing the generated signatures of movement patterns of one body part to the stored signature of all body parts. For example, in accordance with one to many mapping even if a signature is generated for a specific movement pattern of knee, the generated signature is mapped with the stored signatures of movement patterns of all the body parts such as shoulder, ankle, elbow, spine, and the like.

Further, as depicted in step 508 of FIG. 5, the centralized unit 106 is configured to determine, an error indicative of distortion in the movement patterns of the one or more parts of body of the subject in accordance with a difference between the generated signatures and the stored signatures. In an embodiment, the error indicative of distortion is used to quantify the range of motion of the movement patterns of the one or more body parts of the subject. The error indicative of distortion captures change in direction of the range of motion of the one or more body parts. For example, it is assumed that the direction of the range of motion for different movement patterns of knee of a person in normal condition are 15 degrees for hyperextension which may vary to 130 degrees for flexion. However, in a patient affected with arthritis, the direction of range of motion decreases and could be recorded as 20 degrees for hyperextension and 60 degrees for flexion providing an effective arc of only 40 degrees. In an embodiment, the centralized unit 106 is further configured to provide an alert when the error indicative of distortion exceeds a pre-defined threshold, wherein the alert is displayed in at least one of an electronic device handled by the subject. The pre-defined threshold represents an objectively defined value which is assigned as a part of clinical examination of every joint. This can be extended to recording range of motion in the rehabilitation process as well as post-surgical recovery of practically any joint where restoration of range is essential for restoration of function and relief from disability and pain. In an embodiment, the alert could be a text message, an image, a video providing the details of the distortion. The details of distortion may include severity of distortion, status, corrective actions to be taken. In other words, the generated signatures of movement patterns are compared with stored signatures of normal movement patterns to understand abnormal movement patterns based on clinician decided thresholds and may provide output to a treating physician to understand how the patient is affected by a problem or disease.

Figure 9A:
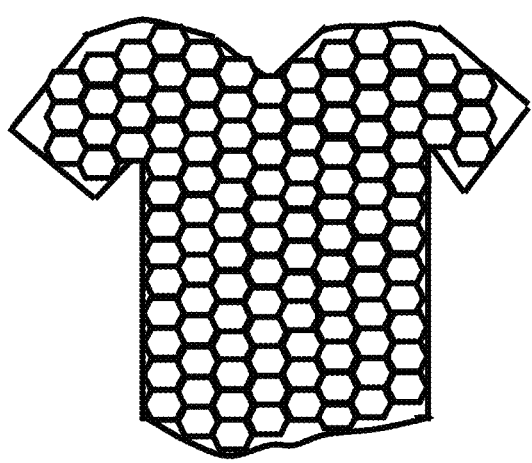
FIGS. 9A through 9F show illustrative examples of articles which can be made using the sensor based wearable fabric design for identifying distortion in movements and quantifying range of motion accordance with some embodiments of the present disclosure.
Figure 9B:
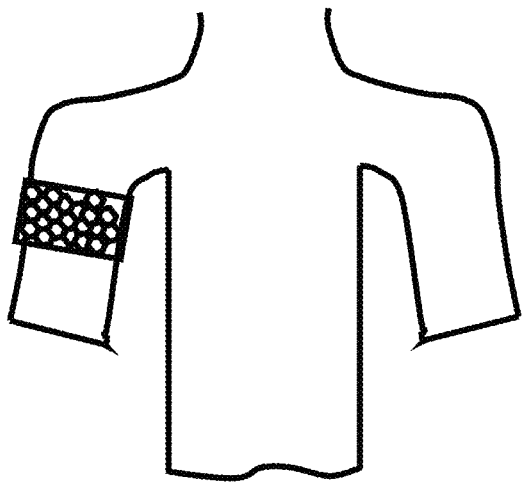
Figure 9C:
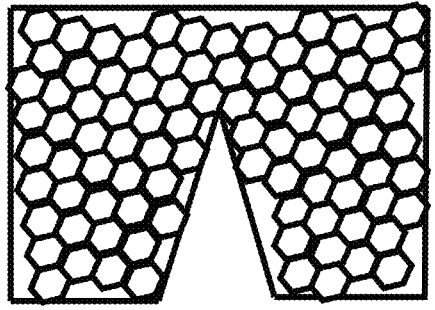
Figure 9D:
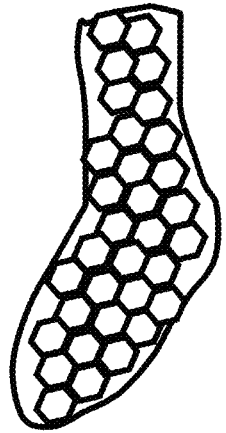
Figure 9E:
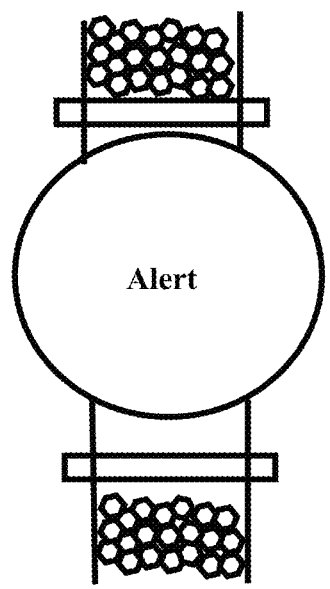
Figure 9F:
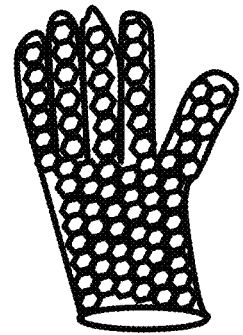

In an embodiment, illustrative articles of clothing woven using the wearable fabric 102 are discussed. FIGS. 9A through 9F show illustrative examples of articles which can be made using the sensor based wearable fabric design for identifying distortion in movements and quantifying range of motion accordance with some embodiments of the present disclosure. The wearable fabric 102 may be used but not limited to form a smart t-shirt or vest, smart arm band, smart shorts, smart socks, smart watch band, and smart gloves as shown in FIG. 9A, FIG. 9B, FIG. 9C, FIG. 9D, FIG. 9E, and FIG. 9F respectively. In an embodiment, the wearable fabric 102 may be completely woven into the clothing article. In another embodiment, the wearable fabric 102 may be woven to be a part of the clothing article. The smart t-shirt or vest can be used to determine shoulder range of motion (ROM), back ROM, thoracic and lumbar range, deformity and posture. In an embodiment, inference of possible defects in posture can be derived by observing signatures of movement patterns while sitting and standing. The smart shorts can be used to study hip movements, trend recovery patterns for patients who have undergone replacement surgeries, and hip reconstruction surgeries. The smart arm band or a knee brace is useful for study of recovery after knee injuries, arthritis patient monitoring and also therapy of patients who have undergone knee replacement surgeries. Similarly, the smart socks or ankle braces can be used to monitor ankle joints and foot deformities. In an embodiment, smart watch band as shown in FIG. 9E or a smart glove shown in FIG. 9F are used to monitor wrist movements. The smart watch band can also be used as a smart watch to work as a display unit for showing the details of the alert sent by the centralized unit 106. However, FIGS. 9A through 9F are only illustrative and the wearable fabric 102 may be used in forming any suitable article of clothing on intended joint/joints which are to be monitored.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of quantification of simple as well as complex multi-axial range of motion, wherein quantification of range of motion becomes challenging for the body parts involving movement in multiple axes leading to inaccurate results. The embodiment, thus provides a sensor based wearable fabric design which has an ability to use deformation of a wearable fabric 102 as a parameter which is reflected as the range of motion, quantify each type of motion, direction of the said motion, and recognize combined movements. For example, in joints like shoulder and spine, multiple joints can also contribute to provide resultant motion whereas pain and restriction may be at one of the joints only. The sensor based wearable fabric design of the present disclosure accurately depicts the motion of these joints record them as they actually occur with the objective of providing a representation as close to body anatomy. The present disclosure facilitates a good analysis of condition of body parts of a subject as well as results of therapeutic intervention on the subject.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A system, comprising:
   a centralized unit;
   a wearable fabric, comprising:
      a plurality of honey-comb structures, wherein each of the honey-comb structure comprising a plurality of adjacently placed hexagon structures,
      wherein each hexagon structure comprising a plurality of optical sensor units with each optical sensor unit placed on each side of the hexagon structure, wherein each of the optical sensor unit includes:
         a coherent light source,
         a Fiber Bragg Grating (FBG),
         a photo detector, and
         a transmitter;

at least a computation unit configured to:
    detect a deformation of a plurality of sides, wherein the plurality of sides corresponds to (i) one hexagon structure or (ii) at least two hexagon structures;
at least a memory to store the detected deformation of the plurality of sides;
wherein the transmitter transmits information related to the detected deformation to the centralized unit,
wherein the centralized unit is configured to:
    receive, the transmitted information related to the detected deformation;
    generate, signatures of movement patterns of one or more parts of body of a subject in accordance with the detected deformation, wherein the signatures of each of the movement patterns is varied for each of the one or more parts of the body, and wherein the signature for a specific movement pattern is generated based on aggregation of the transmitted information related to the detected deformation;
    compare, the generated signatures with stored signatures of movement patterns of the one or more parts of body of the subject, wherein the generated signatures are used to construct an actual trajectory of the one or more parts of body of the subject and the stored signatures includes an expected trajectory of the one or more parts of body of the subject,
        wherein the comparison is performed by a trajectory matching algorithm between the actual trajectory and the expected trajectory, and wherein the trajectory matching algorithm uses a multi-layer perceptron (MLP) for linear approximation of the actual trajectory and the expected trajectory;
    determine, an error indicative of distortion in the movement patterns of the one or more parts of body of the subject in accordance with a difference between the generated signatures and the stored signatures; and
    determine, a range of motion (ROM) of the movement patterns of the one or more parts of the body of the subject, using the error indicative of distortion, wherein the ROM comprises a shoulder ROM, back ROM, thoracic and lumbar ROM, deformity and posture.

2. The system of claim 1, wherein the deformation of the plurality of sides is determined based on a difference in frequency of incident light and reflected light by the Fiber Bragg Grating.

3. The system of claim 1, wherein the information is transmitted from the transmitter to the centralized unit through at least one of (i) a wireless medium channel or (ii) a wired medium channel.

4. The system of claim 1, wherein the centralized unit is further configured to provide an alert when the error indicative of distortion exceeds a pre-defined threshold, and wherein the alert is displayed in an electronic device.

5. The system of claim 4, wherein the step of comparing the generated signatures with the stored signatures includes a one to one mapping or a one to many mapping, wherein the one to one mapping refers to comparing the generated signatures of movement patterns of one body part to the stored signatures of same body part, and the one to many mapping refers to comparing the generated signatures of movement patterns of one body part to the stored signature of all body parts.

6. The system of claim 4, wherein the pre-defined threshold represents an objectively defined value which is assigned as a part of clinical examination of every joint, and wherein the alert comprises a text message, an image, a video providing details of the distortion in the movement patterns of the one or more parts of body of the subject.

7. A method for identifying distortion in movement patterns of a subject, comprising:
    detecting deformation of a plurality of sides in a wearable fabric worn by the subject, wherein the wearable fabric comprising a plurality of honey-comb structures, wherein each of the honey-comb structure comprising a plurality of adjacently placed hexagon structures, and wherein each hexagon structure comprising a plurality of optical sensor units with each optical sensor unit placed on each side of the hexagon structure;
    generating signatures of movement patterns of one or more parts of body of the subject in accordance with the detected deformation, wherein the signatures of each of the movement patterns is varied for each of the one or more parts of the body, and wherein the signature for a specific movement pattern is generated based on aggregation of the transmitted information related to the detected deformation;
    comparing, the generated signatures with stored signatures of the movement patterns of the one or more parts of body of the subject, wherein the generated signatures are used to construct an actual trajectory of the one or more parts of body of the subject and the stored signatures includes an expected trajectory of the one or more parts of body of the subject,
        wherein the comparison is performed by a trajectory matching algorithm between the actual trajectory and the expected trajectory, and wherein the trajectory matching uses a multi-layer perceptron (MLP) for linear approximation of the actual trajectory and the expected trajectory;
    determining, an error indicative of distortion in the movement patterns of the one or more parts of body of the subject in accordance with a difference between the generated signatures and the stored signatures; and
    determining, a range of motion (ROM) of the movement patterns of the one or more parts of the body of the subject, using the error indicative of distortion, wherein the ROM comprises a shoulder ROM, back ROM, thoracic and lumbar ROM, deformity and posture.

8. The method of claim 7, wherein deformation of the plurality of sides is determined based on a difference in frequency of incident light and reflected light by a Fiber Bragg Grating.

9. The method of claim 7, wherein the step of comparing the generated signatures with the stored signatures includes a one to one mapping or a one to many mapping, wherein the one to one mapping refers to comparing the generated signatures of movement patterns of one body part to the stored signatures of same body part, and the one to many mapping refers to comparing the generated signatures of movement patterns of one body part to the stored signature of all body parts.

10. The method of claim 1, wherein the information is transmitted from the transmitter to the centralized unit through at least one of (i) a wireless medium channel or (ii) a wired medium channel.

11. The method of claim 7, wherein the centralized unit provides an alert when the error indicative of distortion exceeds a pre-defined threshold, and wherein the alert is displayed in an electronic device.

12. The method of claim 11, wherein the pre-defined threshold represents an objectively defined value which is assigned as a part of clinical examination of every joint, and wherein the alert comprises a text message, an image, a video providing details of the distortion in the movement patterns of the one or more parts of body of the subject.

13. One or more non-transitory computer readable mediums for identifying distortion in movement patterns of a subject comprising one or more instructions which when executed by one or more hardware processors cause:

detecting deformation of a plurality of sides in a wearable fabric worn by the subject, wherein the wearable fabric comprising a plurality of honey-comb structures, wherein each of the honey-comb structure comprising a plurality of adjacently placed hexagon structures, and wherein each hexagon structure comprising a plurality of optical sensor units with each optical sensor unit placed on each side of the hexagon structure;

generating signatures of movement patterns of one or more parts of body of the subject in accordance with the detected deformation, wherein the signatures of each of the movement patterns is varied for each of the one or more parts of the body, and wherein the signature for a specific movement pattern is generated based on aggregation of the transmitted information related to the detected deformation;

comparing, the generated signatures with stored signatures of the movement patterns of the one or more parts of body of the subject, wherein the generated signatures are used to construct an actual trajectory of the one or more parts of body of the subject and the stored signatures includes an expected trajectory of the one or more parts of body of the subject, wherein the comparison is performed by a trajectory matching algorithm between the actual trajectory and the expected trajectory, and wherein the trajectory matching uses a multi-layer perceptron (MLP) for linear approximation of the actual trajectory and the expected trajectory;

determining, an error indicative of distortion in the movement patterns of the one or more parts of body of the subject in accordance with a difference between the generated signatures and the stored signatures; and determining, a range of motion (ROM) of the movement patterns of the one or more parts of the body of the subject, using the error indicative of distortion, wherein the ROM comprises a shoulder ROM, back ROM, thoracic and lumbar ROM, deformity and posture.

* * * * *